US012603185B1

(12) United States Patent
Liu et al.

(10) Patent No.: US 12,603,185 B1
(45) Date of Patent: Apr. 14, 2026

(54) SCIENTIFIC CLINICAL DIFFUSION NETWORK

(71) Applicant: IQVIA Inc., Parsippany, NJ (US)

(72) Inventors: Yanping Liu, Harleysville, PA (US);
Steve Eichert, Jenkintown, PA (US);
Yong Cai, Marina, CA (US);
Vishwaraj Dilesh Doshi, Farmington
Hills, MI (US); Tong Wu, North Wales,
PA (US); Emily Zhao, Wayne, PA (US)

(73) Assignee: IQVIA INC., Durham, NC (US)

( * ) Notice: Subject to any disclaimer, the term of this
patent is extended or adjusted under 35
U.S.C. 154(b) by 33 days.

(21) Appl. No.: 18/778,330

(22) Filed: Jul. 19, 2024

(51) Int. Cl.
*G16H 50/70* (2018.01)
*G16H 10/60* (2018.01)

(52) U.S. Cl.
CPC ............. *G16H 50/70* (2018.01); *G16H 10/60*
(2018.01)

(58) Field of Classification Search
CPC ............................... G16H 50/70; G16H 10/60
See application file for complete search history.

(56) References Cited

U.S. PATENT DOCUMENTS

| | | | | |
|---|---|---|---|---|
| 11,923,074 B2 | 3/2024 | Li et al. | | |
| 2012/0179002 A1* | 7/2012 | Brunetti | ................. | G16H 20/00 |
| | | | | 600/300 |
| 2015/0170295 A1* | 6/2015 | Shen | ...................... | G06Q 10/40 |
| | | | | 705/319 |

| | | | | |
|---|---|---|---|---|
| 2015/0213233 A1* | 7/2015 | Fleming | ................. | G16H 10/20 |
| | | | | 705/2 |
| 2020/0334566 A1* | 10/2020 | Vianu | ..................... | G16H 50/70 |
| 2020/0411133 A1* | 12/2020 | Xu | ........................... | G16H 50/80 |
| 2021/0098135 A1* | 4/2021 | Frings | .................... | G16H 80/00 |
| 2022/0138651 A1* | 5/2022 | Ramaswamy | ......... | G06Q 50/01 |
| | | | | 705/7.13 |

(Continued)

OTHER PUBLICATIONS

Ramesh et al., "Multi-relational Influence Models for Online Pro-
fessional Networks," ACM. 978-1-4503-4951-2/17/08; DOI: 10.1145/
3106426.3106531. (Year: 2017) (Year: 2017).*

(Continued)

*Primary Examiner* — Sun M Li
(74) *Attorney, Agent, or Firm* — Troutman Pepper Locke
LLP

(57) ABSTRACT

Methods, systems, and apparatus, including computer pro-
grams encoded on computer storage media, for generating a
heterogenous network and determining diffusion weights of
scientific evidence in the heterogenous network. The com-
puter obtains clinical data associated with a clinical network
of healthcare providers and scientific data associated with a
scientific network of scientists. The computer generates a
first graph network representing the clinical network and a
second graph network representing the scientific network.
The computer identifies a first set of target nodes in the first
graph network representing clinical leaders, and a second set
of target nodes in the second graph network representing
scientific leaders. The computer predicts links connecting
the first graph network to the second graph network and
generates a heterogenous network with nodes from the first
graph network and from the second graph network, and the
links connecting the first graph network to the second graph
network.

20 Claims, 10 Drawing Sheets

(56) References Cited

U.S. PATENT DOCUMENTS

| | | | | |
|---|---|---|---|---|
| 2023/0072095 A1* | 3/2023 | Krüger | .................. | G16H 70/20 |
| 2025/0349407 A1* | 11/2025 | Crabtree | ............... | A61B 34/30 |

OTHER PUBLICATIONS

Thomas W. Valente, Social network thresholds in the diffusion of innovations, Social Networks, vol. 18, Issue 1, 1996, pp. 69-89, ISSN 0378-8733, https://doi.org/10.1016/0378-8733(95)00256-1. (https://www.sciencedirect.com/science/article/pii/0378873395002561) (Year: 1996).*

A. Arleo, W. Didimo, G. Liotta, S. Miksch and F. Montecchiani, "Influence Maximization With Visual Analytics," in IEEE Transactions on Visualization and Computer Graphics, vol. 28, No. 10, pp. 3428-3440, Oct. 1, 2022, doi: 10.1109/TVCG.2022.3190623. (Year: 2022).*

Influence Activation Model: A New Perspective in Social Influence Analysis and Social Network Evolution by Yang Yang, Nitesh V. Chawla, Ryan N. Lichtenwalter, and Yuxiao Dong. Nov. 14, 2021, arXiv:1605.08410v1 [physics.soc-ph] May 26, 2016. (Year: 2016).*

M. Rostami, M. Oussalah, K. Berahmand and V. Farrahi, "Community Detection Algorithms in Healthcare Applications: A Systematic Review," in IEEE Access, vol. 11, pp. 30247-30272, 2023, doi: 10.1109/ACCESS.2023.3260652. (Year: 2023).*

Moukarzel S, Rehm M, Del Fresno M, Daly AJ. Diffusing science through social networks: The case of breastfeeding communication on Twitter. PLoS One. Aug. 13, 2020;15(8):e0237471. doi: 10.1371/journal.pone.0237471. PMID: 32790712; PMCID: PMC7425887. (Year: 2020).*

ZionMarketResearch.com [online], "Key Opinion Leader Management Market Size, Share, Growth Report 2032," Mar. 2023, retrieved on Feb. 20, 2025, retrieved from URL <https://www.zionmarketresearch.com/report/key-opinion-leader-management-market>, 14 pages.

* cited by examiner

Figure 4A:
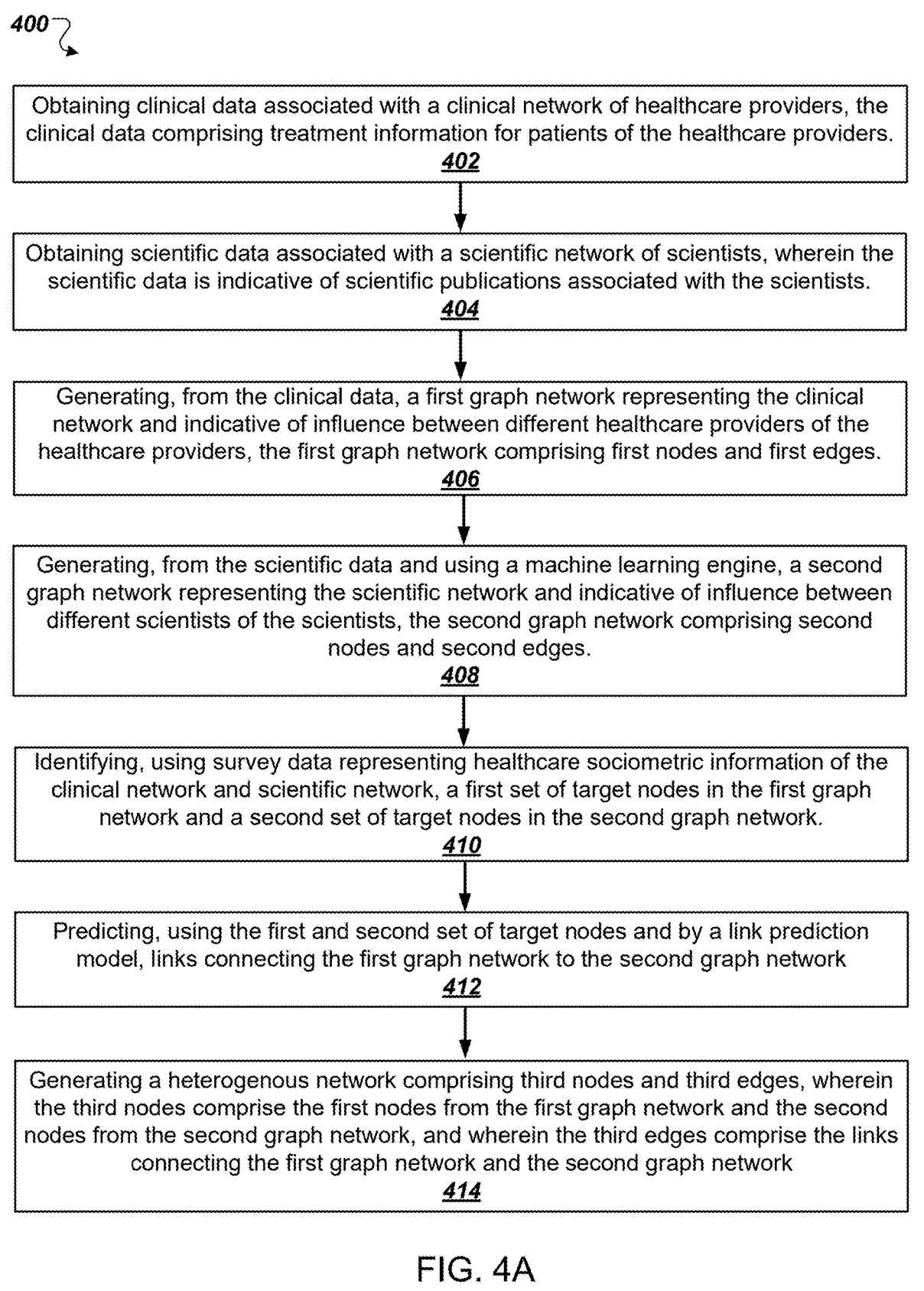

400

Obtaining clinical data associated with a clinical network of healthcare providers, the clinical data comprising treatment information for patients of the healthcare providers.
*402*

Obtaining scientific data associated with a scientific network of scientists, wherein the scientific data is indicative of scientific publications associated with the scientists.
*404*

Generating, from the clinical data, a first graph network representing the clinical network and indicative of influence between different healthcare providers of the healthcare providers, the first graph network comprising first nodes and first edges.
*406*

Generating, from the scientific data and using a machine learning engine, a second graph network representing the scientific network and indicative of influence between different scientists of the scientists, the second graph network comprising second nodes and second edges.
*408*

Identifying, using survey data representing healthcare sociometric information of the clinical network and scientific network, a first set of target nodes in the first graph network and a second set of target nodes in the second graph network.
*410*

Predicting, using the first and second set of target nodes and by a link prediction model, links connecting the first graph network to the second graph network
*412*

Generating a heterogenous network comprising third nodes and third edges, wherein the third nodes comprise the first nodes from the first graph network and the second nodes from the second graph network, and wherein the third edges comprise the links connecting the first graph network and the second graph network
*414*

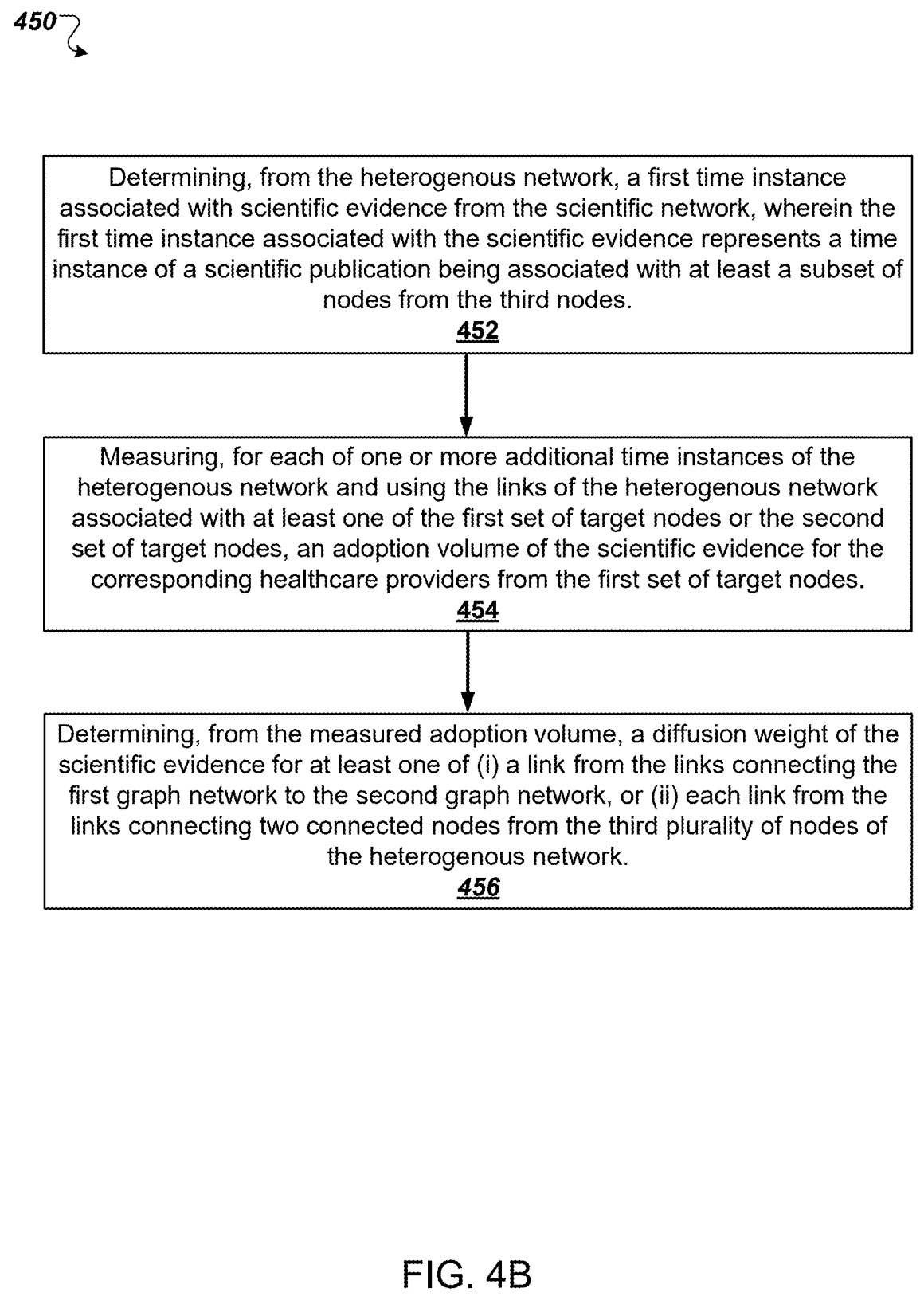

Determining, from the heterogenous network, a first time instance associated with scientific evidence from the scientific network, wherein the first time instance associated with the scientific evidence represents a time instance of a scientific publication being associated with at least a subset of nodes from the third nodes.
452

Measuring, for each of one or more additional time instances of the heterogenous network and using the links of the heterogenous network associated with at least one of the first set of target nodes or the second set of target nodes, an adoption volume of the scientific evidence for the corresponding healthcare providers from the first set of target nodes.
454

Determining, from the measured adoption volume, a diffusion weight of the scientific evidence for at least one of (i) a link from the links connecting the first graph network to the second graph network, or (ii) each link from the links connecting two connected nodes from the third plurality of nodes of the heterogenous network.
456

FIG. 4B

SCIENTIFIC CLINICAL DIFFUSION NETWORK

TECHNICAL FIELD

This specification relates to healthcare data stored in graph networks.

BACKGROUND

The healthcare industry includes various academic and clinical communities with members that have different types of roles in the healthcare industry. Each community can have members with varying levels of influence regarding healthcare administration, such as how to treat certain ailments or conditions. A community member can influence members in their own community and/or members in a different community through evidence, clinical data, and other types of data related to healthcare.

SUMMARY

The technology described in this specification is an approach to quantify and measure influence and adoption of evidence throughout scientific networks, clinician networks, or some combination thereof. In particular, the disclosed technology measures the adoption of scientific evidence in the healthcare industry by processing both scientific data sources and clinical data sources, while considering the overlap between communities. The disclosed technology incorporates community overlap in the healthcare industry by communities are often separated by practice type (e.g., academic, clinical), and constructs a heterogenous network that provides a comprehensive, accurate quantification of knowledge diffusion from scientific leaders to clinical leaders or vice-versa. The heterogenous network allows for modeling of knowledge diffusion between different types of healthcare provider communities (referred to as "subnetworks" in a heterogenous network), allowing for cross-linking between the two types of communities. Thus, the disclosed technology provides an accurate quantification of the diffusion and impact of scientific evidence on the clinical network, and/or the diffusion and impact of clinical data on the scientific network, by modeling influence of members in each type of network regardless of the type of practiced performed by the healthcare provider. The healthcare providers (HCPs) can include scientists, clinicians, and other types of healthcare professionals in the industry.

A graph network can be used to represent the relationships between members in a scientific or clinical communities, such as the influence of one member on another member in the same community. A first graph network representing the scientific community (also referred to as a "scientific network") in the healthcare industry includes nodes to represent scientists and edges connecting pairs of nodes to represent relationships between scientists that are represented by the connected nodes. Similarly, a second graph network representing the clinical community (also referred to as a "clinical network") in the healthcare industry, includes nodes representing clinicians and edges connecting the nodes to represent relationships between clinicians that are represented by the connected nodes. Each type of community in the healthcare industry can include key opinion leaders (also referred to as "KOLs") who have a substantial amount of influence over other members in their community. For example, scientists influence their colleagues by sharing scientific evidence through papers, publications, presentations, etc., whereas clinical practitioners influence their colleagues by sharing clinical data through their treatment decisions, early adoptions of new therapies, referrals, and other types of patient-related data.

The techniques described in this specification relate to a method, system, and apparatus including computer programs encoded on computer storage media, for quantifying and measuring the influence of scientific evidence in a heterogenous network representing both scientific and clinician communities in the healthcare industry. The heterogenous network includes the nodes from a first graph network representing a clinical network of healthcare providers (also referred to as "clinicians") and nodes from of a second graph network representing a scientific network of scientists. The techniques for generating the heterogenous network include identifying a set of target nodes for each graph network that represent the key opinion leaders of the respective healthcare community, and generating, using a prediction model, links representing connections from the target nodes between the two different graph networks that represent the two different communities. The resulting heterogenous network can be used as a model to determine diffusion weights indicating how likely scientific evidence is to propagate from one node to the next node (e.g., from scientist to scientist, scientist to clinician), e.g., by measuring adoption volume of scientific evidence over a period of time.

The first graph network representing the clinical network and the second graph network representing the scientific network are generated from clinical data and scientific data, respectively. Clinical data can include data related to healthcare provider care administered to patients, such as medical claims, prescription claims, demographic data, etc. Scientific data can include data related to scientific studies by scientists, such as grants, presentations, publications, treatment guidelines, etc. Both the clinical data and the scientific data are processed by an intra-network link generator to identify nodes and edges of the respective networks.

The disclosed technology leverages a natural language processing (NLP) model and/or large language model (LLM) to generate mappings that map pieces of scientific evidence (e.g., publications) by scientists across different data domains to the scientists represented in nodes of the scientific network. The mappings allow for cross-referencing of scientific evidence and an exhaustive search for evidence associated with scientists in the scientific network. While clinical data and scientific data can be used to generate the heterogenous network, survey data representing sociometric information about the members in either or both communities can be used to identify the target nodes of the heterogenous network. The target nodes represent key opinion leaders in each network, which are more likely to have inter-network links predicted by the predicted model to connect the two seeming disparate networks, forming a heterogenous network that allows for efficient diffusion modeling of scientific information. Further, the disclosed technology can also leverage data related to nodes (e.g., node attributes) in the heterogenous network to identify the target nodes (e.g., key opinion leaders).

The diffusion network system provides numerous advantages by generating a heterogenous network and modeling diffusion of scientific information. The heterogenous network allows for a quantification of the adoption of a particular piece of scientific evidence, by measuring treatment decisions of healthcare providers in the clinical network. The treatment decisions made by healthcare providers over a period of time allow for a determination of a diffusion weight representing the spread of the particular scientific evidence. By quantifying how scientific evidence is spread within the heterogeneous network, the heterogenous network allows for a computing device to identify more efficient paths in the network, relative to other paths in the network. A first path can be more efficient than another path in the network if the traversal of nodes in the first path that indicate information is more likely to spread faster (e.g., indicated by higher diffusion weights) than if a traversal of nodes in a different path is taken. The diffusion weights are a quantification of a relationship between two disparate networks that otherwise would have been obscured by processing the networks separately. The diffusion weights of the heterogenous network also allow for modeling to identify the most efficient path to share scientific evidence, e.g., identifying key opinion leaders with higher weights to share breakthroughs in medical treatment. The identification of the key opinion leaders allows for the key opinion leaders to be targeted as early adopters for new pharmaceutical medications, medical devices, treatments, and/or medical procedures, to encourage the diffusion of new scientific advances, thereby improving patient outcomes.

The heterogenous network also provides a correlation of scientific evidence from scientists to the trends of treatment patterns by healthcare providers to quantify impact of new scientific evidence. In this way, the heterogenous network allows for a determination of treatment adoption, prescriber behaviors, and scientific influencers within the disparate networks to accurately quantify influence from key opinion leaders in the scientific and clinical networks. In contrast to approaches that independently model influence, diffusion modeling through the heterogenous network connects the scientific and clinical networks but quantifies both inter-network diffusion (e.g., diffusion of evidence within a network) and intra-network diffusion (e.g., diffusion of evidence between different subnetworks or networks). The heterogenous network also allows for the simulation of scientific evidence (e.g., historical diffusion of existing evidence, predicted or estimated diffusion for new evidence). The simulation of scientific evidence propagating throughout the heterogenous network allows for the improved utilization of resources, by identifying key opinion leaders with influence to be targeted as early adopters of the scientific evidence and spreading the scientific evidence more efficiently, e.g., compared to approaches that do not account for influence of members of the healthcare community represented by the heterogenous network.

The diffusion network system leverages one or both of an NLP model or an LLM to process clinical and scientific data into networks, a link prediction model to form inter-network links between the networks for generating the heterogenous network, and an opinion dynamics model trained to learn inter-network diffusion rates between nodes (e.g., scientists and healthcare providers/clinicians) in the heterogenous network. Each of the models is configured to perform specific tasks to model diffusion rates, thus providing a computing system equipped with such models to achieve substantive improvements in computational processing, e.g., compared to a single machine learning model configured to perform multiple types of inference tasks. Rather than using a single model to perform all of the different types of inference tasks (e.g., generating networks, generating the heterogenous networks, performing natural language processing on natural language documents such as scientific evidence), the disclosed technology utilizes different types of models that are each uniquely trained to efficiently perform specific types of tasks (e.g., compared to one model performing all of the tasks) for measuring the diffusion of scientific evidence in a heterogenous network. For example, utilizing one or both of NLP models or LLMs allow for efficient processing of language-based data, as many types of scientific data and clinical data include natural language documents. The link prediction model is trained to identify links between networks, to efficiently perform feature extraction of data represented in the nodes of the networks and generate predictions from the feature data. Lastly, the opinion dynamics model is trained and configured to estimate dissemination of scientific evidence and efficiently provides diffusion weights.

In one general aspect, a method includes: obtaining clinical data associated with a clinical network of healthcare providers. The clinical data includes treatment information for patients of the healthcare providers. The method includes obtaining scientific data associated with a scientific network of scientists. The scientific data is indicative of scientific publications associated with the scientists. The method includes generating, from the clinical data, a first graph network representing the clinical network and indicative of influence between different healthcare providers of the healthcare providers. The first graph network includes first nodes and first edges, each first node representing a corresponding healthcare provider from the healthcare providers, each first edge connecting two first nodes and indicative of influence between the corresponding healthcare providers of the connected first nodes. The method includes generating, from the scientific data and using a machine learning engine, a second graph network representing the scientific network and indicative of influence between different scientists of the scientists. The second graph network includes second nodes and second edges, each second node representing a corresponding scientist from the scientists, each second edge connecting two second nodes and indicative of influence between the corresponding scientists of the connected second nodes. The method includes identifying, using survey data representing healthcare sociometric information of the clinical network and scientific network, a first set of target nodes in the first graph network and a second set of target nodes in the second graph network. Each node in the first set of target nodes represents a clinical leader in the clinical network, and each node in the second set of target nodes represents a scientific leader in the scientific network. The method includes predicting, using the first and second set of target nodes and by a link prediction model, links connecting the first graph network to the second graph network. The method includes generating a heterogenous network that includes third nodes and third edges. The third nodes include the first nodes from the first graph network and the second nodes from the second graph network, and the third edges include the links connecting the first graph network and the second graph network.

Other embodiments of this and other aspects of the disclosure include corresponding systems, apparatus, and computer programs, configured to perform the actions of the methods, encoded on computer storage devices. A system of one or more computers can be configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The foregoing and other embodiments can each optionally include one or more of the following features, alone or in combination. For example, one embodiment includes all the following features in combination.

In some implementations, the method includes determining, from the heterogenous network, a first time instance associated with scientific evidence from the scientific network. The first time instance associated with the scientific evidence represents a time instance of a scientific publication being associated with at least a subset of nodes from the third nodes. The method can include measuring, for each of one or more additional time instances of the heterogenous network and using the links of the heterogenous network associated with at least one of the first set of target nodes or the second set of target nodes, an adoption volume of the scientific evidence for the corresponding healthcare providers from the first set of target nodes. The method can include determining, from the measured adoption volume, a diffusion weight of the scientific evidence for at least one of (i) a link from the links connecting the first graph network to the second graph network, or (ii) each link from the links connecting two connected nodes from the third plurality of nodes of the heterogenous network.

In some implementations, measuring adoption volume of the scientific evidence includes measuring a number of treatment decisions for the patients of the healthcare providers in the clinical network.

In some implementations, the method includes configuring, by one or more computing devices, the heterogenous network as a model to generate a time-series analysis of adoption of one or more of (i) a piece of scientific evidence, or (ii) a medication, by at least a subset of the healthcare providers or the scientists represented by the third nodes of the heterogenous network. The method can include generating, by the model using the input, an output including the time-series analysis of adoption volume from the at least subset of the third nodes. The time period can be is a historical time period that occurs prior to the first time instance. The time period can be a future time period that occurs after the first time instance. In some implementations, the model is configured as simulator of adoption volume. The method can include identifying, from the output, the subset of the third plurality of the heterogeneous network having a diffusion rate at least a threshold value.

In some implementations, generating the second graph network includes generating, by the machine learning engine, one or more mappings between the scientific publications associated with the scientists and the healthcare providers of the clinical network. Each of the one or more mappings represents an influence of a respective scientific publication on the respective healthcare provider.

In some implementations, the clinical data is obtained from a plurality of clinical data sources, including at least one of (i) medical claims, (ii) prescription claims, (iii) healthcare provider demographic data, (iv) medical products, or (v) medical procedures.

In some implementations, the scientific data is obtained from a plurality of scientific data sources, including at least one of (i) clinical trials, (ii) research studies, (iii) patents, (iv) grants, (v) conference presentations, (vi) publications, (vii) treatment guidelines.

In some implementations, the survey data is obtained from surveys of one or both of (i) at least a first subset of the healthcare providers of the clinical network, or (ii) at least a second subset of the scientists of the scientific network. In some implementations, the one or more mappings are stored in a data warehouse.

In some implementations, the first graph network of the clinical network includes one or more identified clinical subnetworks, each identified clinical subnetwork being one of (i) a patient sharing network, (ii) a referral network, (iii) an alumni network, (iv) a referral network, or (v) an advice peer network.

In some implementations, the second graph network of the scientific network includes one or more identified scientific subnetworks, each identified scientific subnetwork being one of (i) a co-authorship network, (ii) a citation network, (iii) a co-trial participants network, or (iv) co-conference presenters network.

In some implementations, the machine learning engine includes at least one of (i) a large language model, or (ii) a natural language processing model.

In some implementations, the first graph network and the second graph network are bipartite graphs of the heterogenous network.

In some implementations, the clinical leader is a healthcare provider from the clinical network with an amount of influence that exceeds a first threshold value.

In some implementations, the scientific leader is a scientist from the scientific network with an amount of influence that exceeds a second threshold value.

In one general aspect, a scientific clinical diffusion system includes a computing device comprising at least one processor and a memory communicatively coupled to the at least one processor, the memory storing instructions which, when executed by the at least one processor, cause the at least one processor to perform operations. The operations include obtaining clinical data associated with a clinical network of healthcare providers. The clinical data includes treatment information for patients of the healthcare providers. The operations include obtaining scientific data associated with a scientific network of scientists. The scientific data is indicative of scientific publications associated with the scientists. The operations include generating, from the clinical data, a first graph network representing the clinical network and indicative of influence between different healthcare providers of the healthcare providers. The first graph network includes first nodes and first edges, each first node representing a corresponding healthcare provider from the healthcare providers, each first edge connecting two first nodes and indicative of influence between the corresponding healthcare providers of the connected first nodes. The operations include generating, from the scientific data and using a machine learning engine, a second graph network representing the scientific network and indicative of influence between different scientists of the scientists. The second graph network includes second nodes and second edges, each second node representing a corresponding scientist from the scientists, each second edge connecting two second nodes and indicative of influence between the corresponding scientists of the connected second nodes. The operations include identifying, using survey data representing healthcare sociometric information of the clinical network and scientific network, a first set of target nodes in the first graph network and a second set of target nodes in the second graph network. Each node in the first set of target nodes represents a clinical leader in the clinical network, and each node in the second set of target nodes represents a scientific leader in the scientific network. The operations include predicting, using the first and second set of target nodes and by a link prediction model, links connecting the first graph network to the second graph network. The operations include generating a heterogenous network that includes third nodes and third edges. The third nodes include the first nodes from the first graph network and the second nodes from the second graph network, and the third edges include the links connecting the first graph network and the second graph network.

In one general aspect, a non-transitory computer-readable storage device storing instructions that when executed by one or more processors of a computing device cause the one or more processors to perform operations. The operations include obtaining clinical data associated with a clinical network of healthcare providers. The clinical data includes treatment information for patients of the healthcare providers. The operations include obtaining scientific data associated with a scientific network of scientists. The scientific data is indicative of scientific publications associated with the scientists. The operations include generating, from the clinical data, a first graph network representing the clinical network and indicative of influence between different healthcare providers of the healthcare providers. The first graph network includes first nodes and first edges, each first node representing a corresponding healthcare provider from the healthcare providers, each first edge connecting two first nodes and indicative of influence between the corresponding healthcare providers of the connected first nodes. The operations include generating, from the scientific data and using a machine learning engine, a second graph network representing the scientific network and indicative of influence between different scientists of the scientists. The second graph network includes second nodes and second edges, each second node representing a corresponding scientist from the scientists, each second edge connecting two second nodes and indicative of influence between the corresponding scientists of the connected second nodes. The operations include identifying, using survey data representing healthcare sociometric information of the clinical network and scientific network, a first set of target nodes in the first graph network and a second set of target nodes in the second graph network. Each node in the first set of target nodes represents a clinical leader in the clinical network, and each node in the second set of target nodes represents a scientific leader in the scientific network. The operations include predicting, using the first and second set of target nodes and by a link prediction model, links connecting the first graph network to the second graph network. The operations include generating a heterogeneous network that includes third nodes and third edges. The third nodes include the first nodes from the first graph network and the second nodes from the second graph network, and the third edges include the links connecting the first graph network and the second graph network.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 4A is a flow diagram that illustrates an example of a process for generating heterogeneous networks for measuring diffusion of scientific information.

FIG. 4B is a flow diagram that illustrates an example of a process for determining diffusion of scientific information throughout different healthcare networks.

Like reference numbers and designations in the various drawings indicate like elements. The components shown here, their connections and relationships, and their functions, are meant to be examples only, and are not meant to limit the implementations described and/or claimed in this document.

DETAILED DESCRIPTION

A diffusion network system can be configured to generate a heterogenous network representing seemingly disparate networks such as scientific communities and clinical communities. The diffusion network system quantifies the impact and the adoption of scientific evidence throughout both networks by constructing a heterogenous network that connects scientific and clinical networks, and predicting links between the two networks that otherwise would be obscured. The diffusion network system generates inter-links between two disparate (e.g., seemingly disconnected) networks to form the heterogeneous network, while intra-links of each individual network are maintained in the heterogeneous network. The diffusion network system is configured to measure adoption of scientific evidence (e.g., across one or more instances of time) throughout the heterogenous network through the adoptions of related therapies, medications, treatment decisions, etc., by members of the healthcare community represented by heterogenous network. By measuring the adopting of scientific evidence and quantifying the influence of members in the healthcare community represented by the heterogenous network, the diffusion network system allows for breakthrough treatments, therapies, procedures, devices, and other forms scientific evidence to be more efficiently adopted by healthcare practitioners. Thus, the diffusion network system provides improved patient outcomes to patients treated by practitioners in the healthcare community.

Figure 1A:
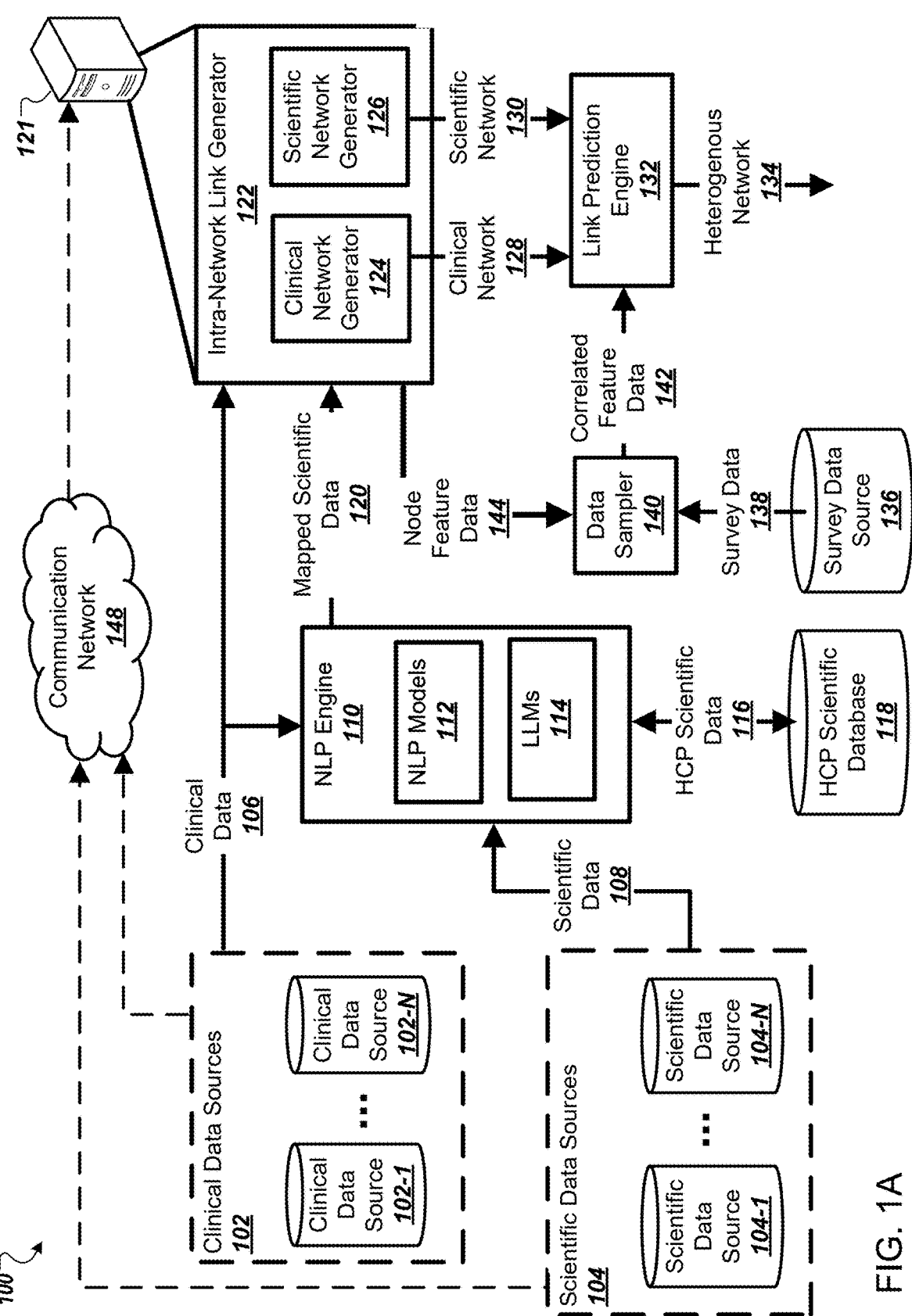
FIG. 1A is a block diagram that illustrate an example of a system for determining diffusion of scientific information among different types of healthcare networks.

FIG. 1A is a block diagram that illustrates an example of a diffusion network system 100 ("system 100") for determining diffusion of scientific information among different types of healthcare networks. The system 100 can be a computing system, device, or collection of devices configured to process input data such as clinical and scientific data, to generate networks, such as clinical networks, scientific networks, and heterogenous networks. As illustrated in FIG. 1, the system 100 includes a computing device 121 with an intra-network link generator 122 configured to generate a clinical network 128 (also referred to as a clinical graph network 128) and a scientific network 130 (also referred to as a scientific graph network 130), from clinical data and scientific data, respectively. FIG. 1A illustrates a number of clinical data sources 102-1 through 102-N (collectively "clinical data sources 102") and a number of scientific data sources 104-1 through 104-N (collectively "scientific data sources 104"). The computing device 121 is communicatively coupled to the clinical data sources 102 and the scientific data sources 104 by a communication network 148. As indicated by the dashed lines illustrated in FIG. 1A, the computing device 121 can be configured to obtain (e.g., wirelessly and/or through a wired connection) data from the clinical data sources 102 and/or the scientific data sources 104. In some implementations, data from external sources such as the clinical data sources 102 and the scientific data sources 104 can be stored in memory storage of the computing device 121.

The system 100 is configured to obtain clinical data 106 from the clinical data sources 102 and scientific data 108 from scientific data sources 104. Clinical data sources 102 can include any source of data that relate to the treatment of patients by clinical healthcare providers, e.g., electronic health records, information systems (for hospitals, clinical trials, laboratories, pharmacies), health information exchanges, registries, clinical trial databases, patient monitoring systems and devices, and public health databases. Examples of data obtained from clinical data sources can include medical claims, prescription claims, treatment information and/or decisions, healthcare records, demographic data (e.g., related to patients, healthcare providers, or some combination thereof), medical products, medical procedures, among others. Clinical data 106 includes the names of clinicians, in which the system 100 is configured to link portions of the clinical data 106 to particular healthcare providers (e.g., clinicians, scientists).

Scientific data sources 104 can include different types of organizations (e.g., research, non-profit, academic, government), agencies, registries, clinical trial databases, journal databases, that provide scientific data 108, such as data related to or from clinical trials, data related to or from research studies, patents, grants, conference presentations, publications, treatment guidelines, among others. The scientific data 108 can include pieces of scientific evidence related to a particular treatment, therapy, medication, etc. Scientific data 108 includes the names of scientists, in which the system 100 is configured to link portions of the scientific data 108 to particular healthcare providers (e.g., clinicians, scientists). Each of the clinical data 106 and the scientific data 108 can include structured and/or unstructured data formats. In some cases, clinical data 106 and scientific data 108 can include metadata for the respective type of data. For example, scientific data 108 can include metadata (e.g., publication metadata) about a piece of scientific evidence (e.g., publication). As another example, clinical data 106 can include metadata (e.g., medical record metadata) for medical records.

The system 100 includes the computing device 121 configured to generate networks based on the respective data provided for each type of network, such as clinical network 128 from clinical data and scientific network 130 from scientific data. A network includes nodes representing an entity (e.g., a scientist, a clinician) and edges (also referred to as "links") connecting two nodes, the connection representing a relationship between the two entities corresponding to the connected nodes. For example, with reference to FIG. 2A, a clinical network 220 includes nodes (e.g., nodes 214, 216) representing clinicians (e.g., clinical healthcare practitioners clinical trial administrators) and edges (e.g., edge 218) representing a relationship between the clinicians. In this context, a link between two clinicians in a clinical network (e.g., clinical network 220) can be a relationship between a first clinician (e.g., node 214) and a second clinician (e.g., node 213 connected to node 214), indicating that the two clinicians belong to the same healthcare organization, have a partnership in a medical practice and/or clinical trial together, belong to the same professional organization, belong to the same referral network, among other types of relationships (e.g., affiliations) between clinicians. Similarly, a scientific network (e.g., scientific network 210) includes nodes (e.g., nodes 204, 205) representing scientists (e.g., principal investigators, staff scientists, laboratory assistants, among other scientific professional roles) and edges (e.g., edge 206) representing a relationship between the scientists. A link (e.g., edge 206) between two scientists (e.g., nodes 204, 205) in a scientific network (e.g., scientific network 210) can be a relationship between a first scientist and a second scientist, indicating that the two scientists belong to the same research organization, academic institution, have a partnership in a research activity (e.g., a study, a grant, an article, a paper publication, a patent, among other types of publications), belong to the same professional organization, belong to the same academic network, among other types of relationships between scientists.

Referring to FIG. 1A, the computing device 121 includes an intra-network link generator 122 configured to generate links within a respective network, such as links between nodes representing clinicians for a clinical network and links between nodes representing scientists for a scientific network. In the implementation illustrated in FIG. 1A, the clinical data 106 can be provided to the intra-network link generator 122 (e.g., retrieved by the computing device 121) to generate intra-network links for the clinical network, whereas the scientific data 108 can be processed by a natural language processing (NLP) engine 110 to generate mapped scientific data 120 prior to generating intra-network links for the scientific network.

The NLP engine 110 is configured to process the scientific data 108 to generate mappings between scientists and pieces of scientific evidence from the scientific data 108. In this way, attribution (e.g., authorship) to different pieces and types of scientific data (e.g., evidence) can be mapped to different scientists in the scientific network. In this way, the NLP engine 110 performs a semantic analysis of different pieces of scientific evidence to increase the accuracy of associating scientific work (e.g., publications, research studies) to the appropriate scientists in the scientific network. For example, an identifier for the same scientist across different publications (e.g., different pieces of scientific evidence) can be recorded differently across different scientific sources, e.g., full name compared to first initial and last name, full name and middle initial compared to first initial, middle initial, and last name. Thus, the NLP engine 110 performs an analysis of the corpus of scientific data to generate mapped scientific data 120 that can more accurately map pieces of scientific evidence to the corresponding scientists. In some cases, the NLP engine 110 also analyzes the clinical data 106 to identify instances of a scientist's name and/or work, which can increase the likelihood of correctly associating (e.g., attributing) a piece of scientific evidence to the scientists. In some cases, the scientific data 108 can be provided to the computing device 121 for the intra-network link generator 122 to generate a scientific network, e.g., without pre-processing the scientific data to generate the mapped scientific data 120. For example, the scientific networks can be generated by analyzing co-authorship of pieces of scientific evidence between two or more scientists, among other types of relationships, e.g., co-presenting, collaboration for a clinical trial.

The NLP engine 110 include NLP models 112 and large language models (LLMs) 114 that can be configured by the NLP engine 110 to analyze the scientific data 108 and associate pieces of scientific evidence to a particular healthcare provider for a scientist network. For example, one or both of the NLP models 112 and the LLMs 114 can be configured by the NLP engine 110 to match pieces of scientific evidence found in the scientific data to particular healthcare providers, by performing a semantic analysis of the pieces of scientific evidence that identifies and classifies entities in a piece of scientific evidence (e.g., keywords, names of medications and/or therapies, citations, names of healthcare providers). The NLP models 112 and the LLMs 114 can be configured to parse through medical texts and documents to perform NLP tasks such as information extraction, author recognition, and HCP-author matching. While both the NLP models 112 and LLMs 114 can be configured to perform NLP tasks, the NLP engine 110 can leverage the LLMs 114 to process scientific data and clinical data in a way that maintains contextual relevance for the respective data, while simplifying processing of the data.

For example, information extraction can include identifying relationship names and relationship data (e.g., other types of information about an affiliation) from publications, clinical trial documents, etc. Author recognition can include standardizing formats for author names across different types of document sources to a single format that can be adopted across the system 100. In some implementations, the NLP engine 110 can be configured to perform matching between HCPs and authors by matching attributes of the HCPs and attributes of authors of scientific evidence based on a number of dimensions. The dimensions can include similarity in geo-location, affiliation, embedding of publication topics, and embedding of medical specialties/expertise. In some implementations, the NLP engine 110 can be configured to perform post-processing on the outputs of NLP models 112 and the LLMs 114 to reduce the likelihood of unmatched HCPs to authorship of a text.

In some cases, the NLP engine 110 leverages clinical data 106 as contextual data for scientific data 108, e.g., to generate the mapped scientific data 120. For example, clinical data 106 collected from medical claims can indicate an identified prescribed medication in the medical claims that can be found (e.g., referenced) by a piece of scientific evidence. In this way, the clinical data 106 can be processed by the NLP engine as additional context for generating mappings between scientific healthcare providers and associated pieces of scientific evidence, thereby increasing the accuracy of a resulting scientific network through mapped scientific data 120. The NLP engine 110 is also configured to communicate with an HCP scientific database 118, which can include a record of scientific healthcare providers. The NLP engine 110 can access records of scientific HCPs to generate the mapped scientific data 120, by reducing inconsistencies in identifying of scientific HCPs across different types and instances of scientific evidence in scientific data 108. The NLP engine 110 can also be configured to update records of the HCP scientific database 118 by providing HCP scientific data 116, which can include modifications such as updating the recorded name of a scientific HCP, adding a new association of a piece of scientific evidence with a scientific HCP, etc.

Referring to the computing device 121 of FIG. 1A, the intra-network link generator 122 can include a respective generator for each type of network. For example, FIG. 1A depicts the intra-network link generator 122 having a clinical network generator 124 for processing clinical data 106, e.g., to generate links between clinicians in the clinical network, and a scientific network generator 126 for processing mapped scientific data 120, e.g., to generate links between scientists in the scientific network. In some implementations, the intra-network link generator 122 includes a single network generator configured to generate respective links for connected nodes for different types of networks.

A network generator (e.g., clinical network generator 124, scientific network generator 126) for the intra-network link generator 121 can be configured to generate nodes for a network based on entities identified in the received data, e.g., the clinical data 106, the mapped scientific data 120. A network generator can perform data pre-processing techniques to identify professionals to be represented as nodes in a graph network, such as clinicians for the clinical graph network 128 and scientists for the scientific graph network 130. A network generator can also be a machine learning model configured to generate graph networks. For example, the network generator can be configured to generate a node in a network for each unique HCP in the network. Each node in a respective network can include an identifier corresponding to the healthcare provider, attributes describing properties of the node (e.g., a degree of the node, a classification label for the node), node metadata (e.g., a timestamp indicating the generation of the node, a timestamp indication the most recent time a node was updated). In some implementations, feature data associated with the healthcare provider (e.g., clinical, scientific) represented by the node can be embedded into a data structure, e.g., an array, a tensor, a feature vector.

The intra-network link generator 122 can generate links (e.g., edges) for a graph network by identifying, for each node, connections to other nodes in the graph network. For example, the intra-network link generator 122 can process a node corresponding with a first healthcare provider in the graph network and identify from data (e.g., clinical data 106, mapped scientific data 120), nodes corresponding to other healthcare providers in the graph network that share the same type of healthcare profession (e.g., connecting nodes between scientists, connecting nodes between clinicians). In some implementations, the intra-network link generator 122 performs an iterative process to evaluate nodes and/or applies a number of rules (e.g., selection criteria) to link two nodes within the same network. In some implementations, the intra-network link generator 122 is configured to determine centrality measures, network connectivity, and/or perform other types of nodal analysis of a graph network to determine the intra-network links for a graph network, e.g., clinical network 128, scientific network 130.

The feature data of nodes of the clinical network 128 and/or the scientific network 130 can be provided to a data sampler 140 as node feature data 144. The data sampler 140 is also configured to receive survey data 138 representing information about the relationships between different members in a network. The information can provide indications of key opinion leaders in a network, which can refer to members in a network with influence in their respective networks and/or across networks. For example, a clinical key opinion leader can be a clinician with a substantive amount of influence in their clinical network and a scientific key opinion leader can be a scientist with a substantive amount of influence in their scientific network. In some cases, scientists can include different types of healthcare providers, although a subset of scientists can be a non-healthcare provider role. Examples of non-healthcare provider roles can include researchers (e.g., doctoral students/candidates, post-doctoral researchers), statisticians (e.g., biostatisticians), among other types of non-healthcare provider roles in the scientific community.

A key opinion leader may develop influence their respective network and/or across networks from their professional experience and/or activities in scientific research, healthcare administration, patient care, clinical trial administration, etc., degree of participation with others in their network, as well as an amount of time spent in their respective field and/or industry.

The survey data 138 can be obtained through surveys, interviews, observational studies, peer ratings and/or nominations, online and/or in-person interactions, among other approaches. The data sampler 140 is configured to correlate the node feature data 144 to the survey data 138, to generate correlated feature data 142. The correlated feature data 142 can include updates to the feature data corresponding to nodes in a graph network, indicating that the node can correspond to a key opinion leader in the network.

Referring to the system 100, FIG. 1A shows the computing device 121 providing the clinical network 128 and the scientific network 130 to a link prediction engine 132, and the data sampler providing the correlated feature data 142 to the link prediction engine 132. The link prediction engine 132 is configured to generate predicted links between the two different types of networks based on feature data, attributes, etc., of the nodes in each network, as well as the correlated featured data 142 derived from the survey data 138. By generating predictions from the correlated feature data 142 in addition the clinical network 128, and the scientific network 130, the link prediction engine 132 can improve a likelihood of generating a link that accurately connects a first node from the first network (e.g., the clinical network) to a second node from a different network than the first network (e.g., the scientific network). The link prediction engine 132 can be configured to perform feature extraction from the nodes of the networks, and in addition to generating the link between two nodes from two different networks, generate a numerical value representing the likelihood of the link between the two nodes. The link prediction engine 132 can generate multiple links between the two networks to generate a heterogenous network 134, e.g., a network that includes two or more different types of networks. Further description of the link prediction engine 132 can be found in reference to FIG. 1B below.

Any of the models depicted in FIG. 1A can be trained by the system 100 using a variety of training techniques to improve the accuracy of inference tasks performed by the respective model. These training techniques can include supervised and unsupervised learning. The models can include any form of boosting techniques such as gradient boosting but can include deep learning techniques for to perform an inference task. For example, an inference task for an NLP model and/or an LLM can include performing text classification, entity identification, machine translation, and other types of semantic analysis. As another example, an inference task for a link prediction engine can include generating links between two or more different types of networks, links within the same network, or some combination thereof. In some examples, a model performs hybrid-learning techniques to improve accuracy of model output. Training processes for the models depicted in FIG. 1A can include any number of iterative processes, each performing a number of iterations to train the model to achieve a target performance value, e.g., an error rate below a threshold value, a generated classification label that matches the ground truth label.

The training of a model can be performed using obtained ground truth data that includes known labels, associations, classifications, etc., coupled with a corresponding input, e.g., some or all of the clinical data, some or all of the scientific data, or some combination thereof. A model can adjust one or more weights or parameters to match estimates or predictions from the to the ground truth data. In some implementations, a model includes one or more fully or partially connected layers. Each of the layers can include one or more parameter values indicating an output of the layers. The layers of the model can generate outputs for which the model can use for performing one or more inference tasks. The models can be validated and tuned through holdout and test techniques, model comparison, and model selection.

As illustrated, the system 100 is deployed on a computing device 121, but can deployed on other types of computing devices, systems, platforms, etc., that can be communicatively coupled to other computing hardware, e.g., by communication network 148. Examples of communication network 148 can include Bluetooth, Wi-Fi, the Internet, etc. In some implementations, a component (e.g., the computing device 121) of the diffusion system 100 is coupled to some or all of the other components (e.g., the NLP engine 110, the HCP scientific database 118, survey data source 136, clinical data sources 102, scientific data sources 104), by a wired connection, wireless connection, etc.

Figure 1B:
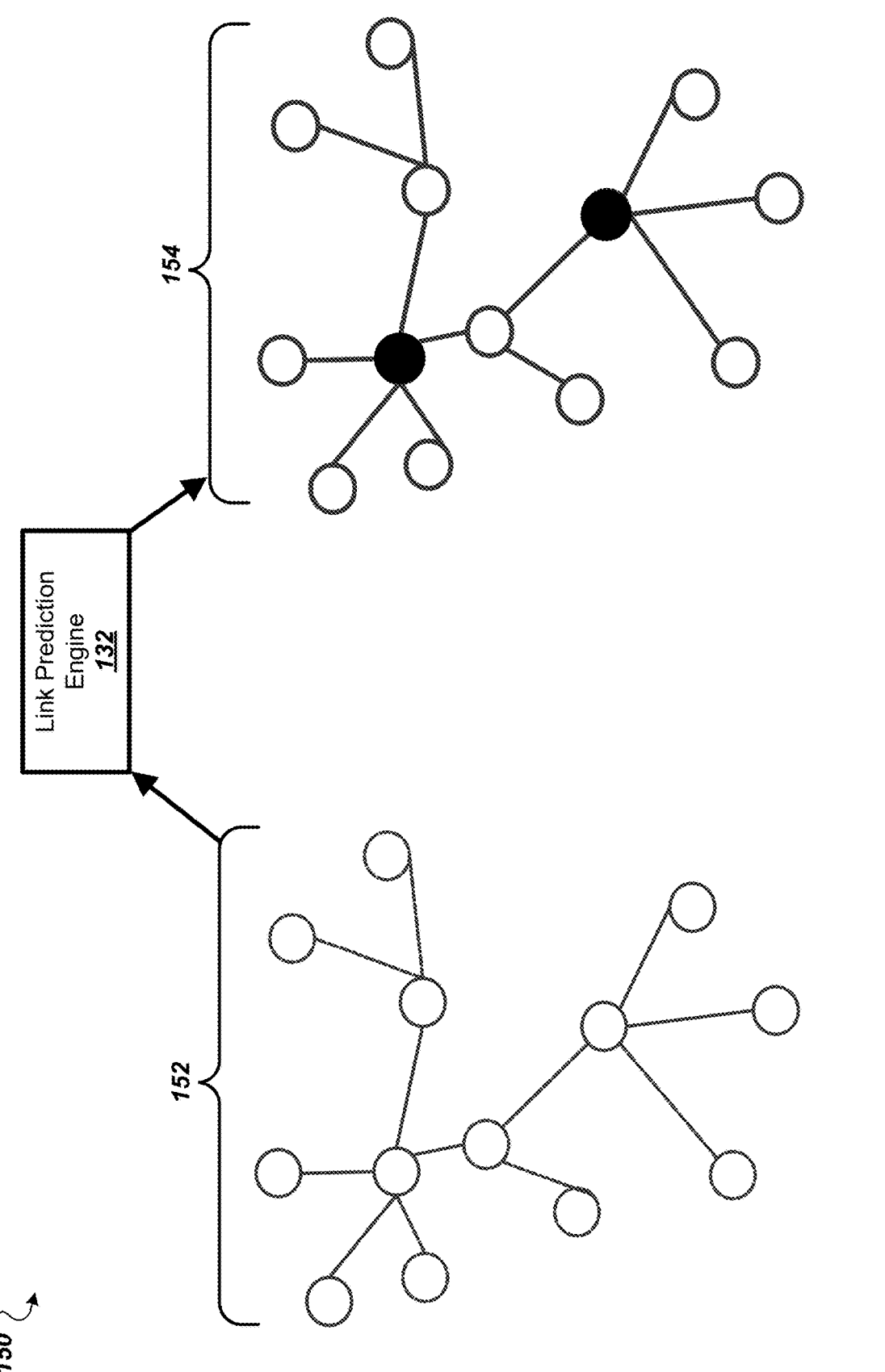
FIG. 1B is a diagram that illustrates an example link prediction engine for generating links between different types of networks in a heterogenous network.

FIG. 1B is a diagram 150 that illustrates the link prediction engine 132 generating links between different types of networks to generate a heterogenous network. The diagram 150 shows an input network 152 of a first type (e.g., a clinical network, a scientific network) with nodes (illustrated as circles with a solid line) representing healthcare providers (e.g., clinicians, scientists) and edges (illustrated as solid lines) representing established connections between the healthcare providers represented by the connected nodes. The diagram 150 shows nodes (illustrated as circles with a dashed line) from a different type of network than the input network 152, indicating nodes from the different type of network that can be potentially linked to the input network 152, e.g., linking candidate nodes to the nodes of the input network 152. For example, the input network 152 can be a clinical network and the link prediction engine 132 can be configured to predict links from nodes of the clinical network to another type of network, e.g., a scientific network. The link prediction engine 132 is configured process feature data of the nodes in the input network 152 and feature data of nodes from a different network type to predict potential links between the nodes of the input network 152 and the nodes from the different network type.

The link prediction engine 132 generates links by mining feature data of nodes from the clinical network 128 and the scientific network 130. Features can include clinical features such as distance, demographics, affiliations, prescribing behavior, payer/payee mix, number of optics, citations, networks, etc. In some cases, feature data can be associated with subnetworks of a respective graph network, e.g., a subset of nodes and edges of the graph network. For example, subnetworks for the input network 152 that is a clinical network can include advice discussion networks, patient sharing/referral networks, affiliation/relationship networks, and alumni networks. Similarly, subnetworks for the input network 152 that is a scientific network can include co-authorship/citation networks, co-trial participant networks, and co-conference speaker networks. Upon predicting links that are likely to connect nodes of different network types, the link prediction engine 132 can generate an output network 154 that includes predicted links connecting candidate nodes from a different network.

In some cases, the predicted links in the output network 154 can include a value indicating a likelihood that the influence between the two connected nodes. Furthermore, the output network 154 can update node features or attributes to indicate that a node corresponds to a key opinion leader, e.g., a target node. Key opinion leaders can be represented as nodes in the output network 154 indicated by circles filled with a solid color. An update to the network can be derived from the correlated feature data 142, based on the survey data 138, survey data source 136, node feature data 144, or some combination thereof. In some cases, key opinion leaders are determined using the clinical data and the scientific data. For example, the scientific data includes a number of publications, presentations, clinical trials, etc., that can be used to identify scientific key opinion leaders. As another example, the clinical data includes a number of treatment decisions, patient referrals, number of patient visits, etc., that can be used to identify clinical key opinion leaders. The survey data 138 can be used to identify peer leaders that are scientists from the scientific network with influence on clinicians in the clinical network.

The system 100 can be configured to analyze adoption volume in each subnetwork of the heterogenous network (e.g., clinical network, scientific network) and can determine weights that indicate adoption of a therapy, scientific evidence, etc., from one subnetwork to another subnetwork of the heterogenous network. For example, the system can quantify the adoption of scientific research within the scientific community, the adoption of therapies (e.g., products, procedures) within the clinical network, and determine the spread of scientific research and/or the therapies through each and/or both of the subnetworks of the heterogenous network (e.g., clinical network, scientific network). The adoption volume can be determined from clinical data sources and scientific data sources that include data related to medical claims. The heterogenous network can be configured to determine (e.g., model) an association between links of the network and adoption volume, and weights can be determined to show correlation between the network link and adoption volume, e.g., based on the claims data.

Figure 2A:
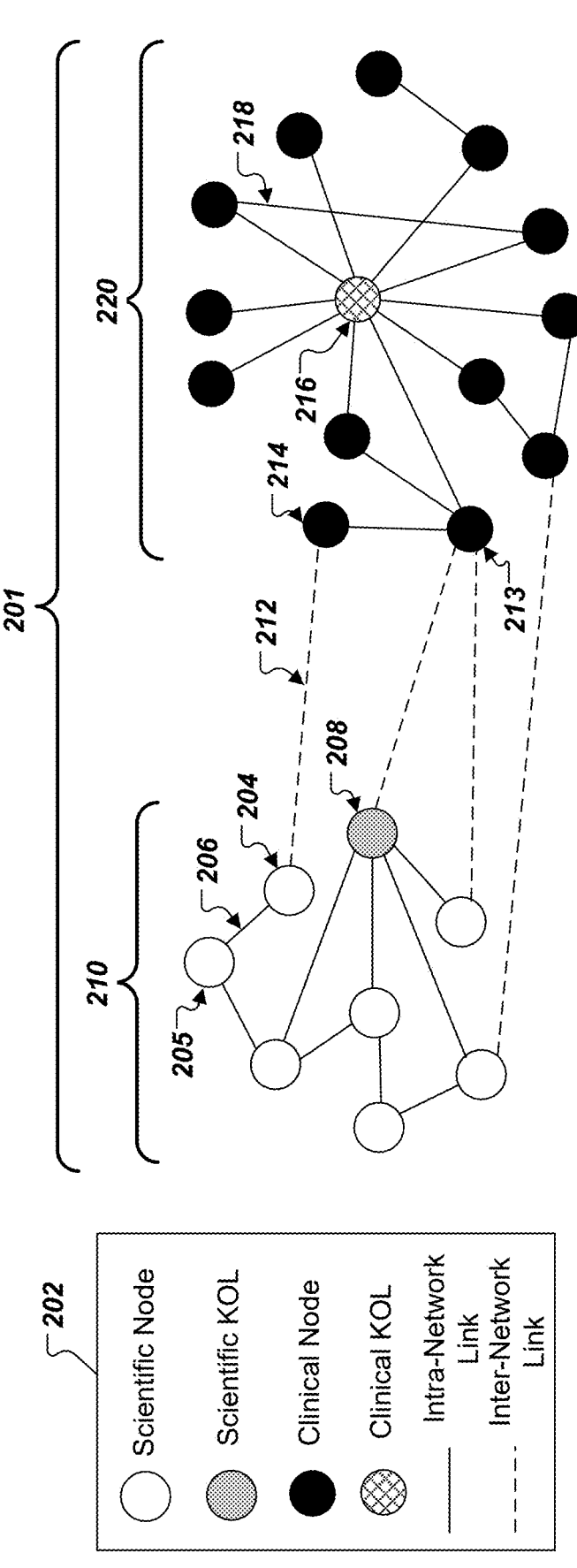
FIG. 2A is a diagram that illustrates an example of a heterogenous network representing different healthcare networks.

FIG. 2A is a diagram 200 that illustrates an example of a heterogenous network 201 representing different healthcare networks. The heterogenous network 201 is an example of the heterogenous network 134 and includes two different types of networks: a scientific network 210 (e.g., scientific network 130) and a clinical network 220 (e.g., clinical network 128). FIG. 2A also shows a legend 202 illustrating different components of the graph networks, e.g., types of nodes and edges. For example, the scientific network 210 a number of scientific nodes illustrated as circles, each node representing a scientist in the scientific network 210. Two scientific nodes 204 and 206 shown in FIG. 2A are illustrated as being connected by an intra-network link 206, e.g., indicating that the scientists represented by the connected scientific nodes 204, 206 have a relationship (e.g., affiliation) with one another. The scientific network 210 also includes a scientific key opinion leader illustrated as a grey circle and indicated as scientific key opinion leader node 208, with a number of links connected the scientific key opinion leader node 208 to other nodes. For example, the scientific key opinion leader node 208 is adjacent to four scientific nodes in the scientific network 210. In some cases, a node representing a key opinion leader can be identified by the system 100 when generating the heterogeneous network from the system 100 processing data related the node, such as attributes, connectivity, etc.

Similarly, the diagram 200 shows the clinical network 220 of the heterogenous network 201 having a number of clinical nodes, indicated by black circles in FIG. 2A. An example clinical node is indicated as clinical node 214 in the clinical network 220. The clinical network 220 also includes a clinical key opinion leader node 216 (illustrated as a circle with a cross-hatching pattern) corresponding to a clinical key opinion leader in the clinical network. The clinical network 220 also includes an intra-network link between two clinical nodes, e.g., an example intra-network link in the clinical network 220 is indicated by intra-network link 218.

The scientific network 210 and the clinical network 220 can be formed into the heterogenous network 201 by generating links connecting the two types of networks. The heterogenous network 201 includes a number of inter-network links generated by the link prediction engine of FIG. 1, e.g., link prediction engine 132. The inter-network links indicated by dashed lines connect the scientific network 210 to the clinical network 220, and an example inter-network link 212 connects scientific node 204 to clinical node 214.

Figure 2B:
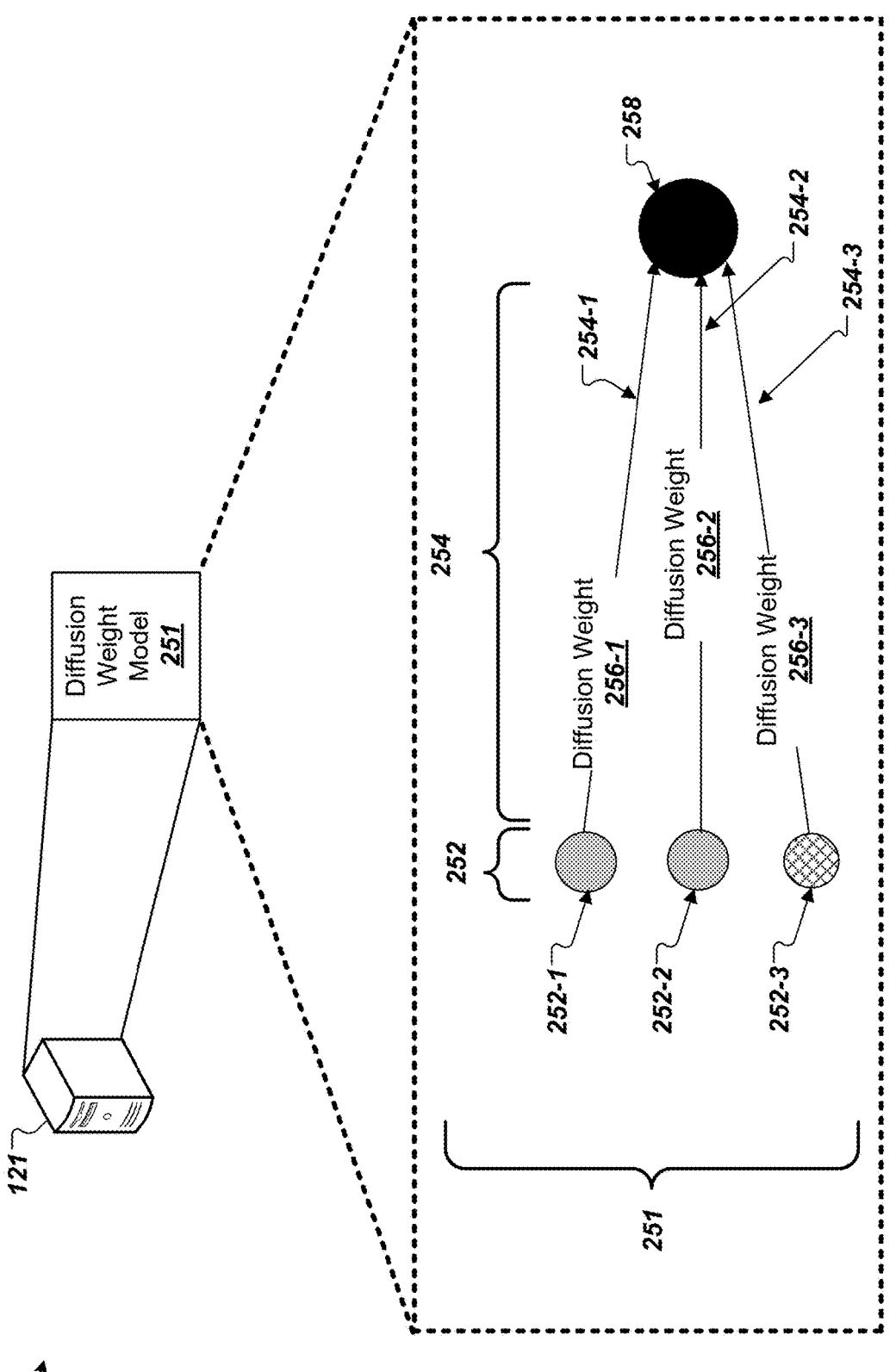
FIG. 2B is a diagram that illustrates an example of diffusion weights for scientific evidence throughout a heterogenous network.

FIG. 2B is a diagram 250 illustrating an example of diffusion weights for scientific evidence throughout a heterogenous network. The diagram 250 shows the computing device 121 of FIG. 1A configured to determine diffusion weights for a subset 253 of a heterogenous network, e.g., heterogenous network 201, which may also be referred to as a subnetwork 253. The computing device 121 includes a diffusion weight model 251 ("also referred to as an "opinion dynamics models 251") that processes data and determines the diffusion of a piece of scientific evidence throughout the heterogenous network. An opinion dynamics model 251 can be trained using time-series scientific data from scientific data sources, such as citations, publications, and other types of scientific activities, and/or time-series clinical data from clinical data sources, such as new-to-brand prescriptions (NBRx data) prescribed by clinicians. The time-series scientific data and/or time-series clinical data can be preprocessed (e.g., normalized) prior to the opinion dynamics models 251 determining scientific-to-clinician rates.

The subnetwork 253 shows scientific key opinion leader nodes 252-1, 252-2, and clinical key opinion leader node 252-3 (collectively "nodes 252") connected to clinical node 258 through links 254. The links 254 include a link 254-1 connecting scientific key opinion leader node 252-1 to clinical node 258, a link 254-2 connecting scientific key opinion leader node 252-2 to clinical node 258, and a link 254-3 connecting clinical key opinion leader node 252-3 to clinical node 258. Each link from the links 254-1 through 254-3 (collectively "links 254") can have a respective diffusion weight representing a likelihood of information transmission between two connected nodes. For example, diffusion weight 256-1 represents the influence of the scientist represented by scientific key opinion leader node 252-1 on the clinician represented by clinical node 258. Similarly, diffusion weight 256-2 represents the influence of scientific key opinion leader node 252-2 on clinical node 258 and diffusion weight 256-3 represents the influence of clinical key opinion leader node 252-3 on clinical node 258.

The diffusion weight model 251 can estimate diffusion of scientific evidence throughout the heterogenous network by applying modeling equations to time-series clinical data and scientific data, then estimating for coefficients representing diffusion rates of information between nodes of the heterogenous network. Examples of time-series clinical data can include metrics for measuring patient prescription behaviors (e.g., prescriptions of a particular medication, therapy, etc.), such as new-to-brand prescriptions (NBRx). For example, the NBRx metric can be a longitudinal analysis of prescription activity of clinicians in the heterogenous network. Examples of time-series scientific data can include metrics related to a number of publications, citations, etc., for a piece of scientific evidence.

Equation (1) below represents a rate of change of clinician opinion adoption $x_i(t)$ for an $i^{th}$ clinical key opinion leader at a time instance t. Equation (2) below represents a rate of change of scientific opinion adoption $y_i(t)$ for an $i^{th}$ scientific key opinion leader at a time instance t. Equations (1) and (2) can be applied to time series data associated with the set of all clinical key opinion leaders $N_c$, time series associated with the set of all scientific key opinion leaders $N_s$, and the combined set of key opinion leaders $\{N_S \cup N_C\}$, e.g., clinical key opinion leaders $N_c$ and scientific key opinion leaders $N_s$.

$$\frac{dx_i(t)}{dt} = (1 - x_i(t)) \sum_{j \in N_C} A_{ji} x_j(t) + (1 - x_i(t)) \sum_{k \in N_s} C_{ki} y_k(t) \quad (1)$$

$$\frac{dy_i(t)}{dt} = (1 - y_i(t)) \sum_{j \in N_s} B_{ji} y_j(t) \quad (2)$$

The diffusion weight model 251 can be configured to solve (e.g., using a number of optimization techniques) for coefficients $A_{ji}$ and $B_{ji}$ in Equation (1) and $C_{ki}$ in Equation (2), through any number of statistical and/or machine learning techniques. The coefficient $A_{ji}$ represents an opinion diffusion rate from a clinical key opinion leader j to a clinical key opinion leader i in the heterogenous network, e.g., a first node representing a first clinical key opinion leader j to a second node representing a second clinical key opinion leader i. The coefficient $A_{ji}$ between two nodes each representing a clinical key opinion leader without an edge connecting the two key opinion leaders is zero. Similarly, the coefficient $B_{ji}$ represents an opinion diffusion rate from a scientific key opinion leader j to a scientific key opinion leader i in the heterogenous network, e.g., a first node representing a first scientific key opinion leader j to a second node representing a second scientific key opinion leader i, and the value of $B_{ji}$ being zero if the two nodes do not have an edge connecting them to each other in the heterogenous network. The coefficient $C_{ki}$ represents an opinion diffusion rate from a scientific key opinion leader j to a clinical key opinion leader i in the heterogenous network, e.g., a first node representing a first scientific key opinion leader j to a second node representing a first clinical key opinion leader i. Similarly, the value of $C_{ki}$ is zero if there is no edge connecting the scientific key opinion leader to the clinical key opinion leader. As described in reference to FIG. 1B above, a link prediction engine can be configured to generate links between two different types of networks or subnetworks, to form a heterogenous network.

For clinical non-key opinion leaders, the clinician opinion adoption $x_i(t)$ can be set to zero to initialize the model, e.g., based on an assumption that of zero influence from non-influential clinicians in the heterogenous network. Similarly, for scientific non-key opinion leaders, the scientific opinion adoption $y_i(t)$ can also be set to zero. The clinician opinion adoption $y_i(t)$ and/or scientific opinion adoption $x_i(t)$ can be normalized to a range of values between 0 and 1, in which 0 represents a lack of adoption of a piece of scientific evidence and 1 represents adoption of the piece of scientific evidence.

The coefficients for equations (1) and (2) (e.g., $A_{ji}$, $B_{ji}$, and $C_{ki}$) can be estimated using a number of statistical and/or machine learning techniques, such as least squares, gradient descent, maximum likelihood estimation, regressions techniques (e.g., Ridge, LASSO, polynomial, Bayesian), among others. Similar to the models described in reference to FIGS. 1A and 1B above, the system 100 can perform a variety of training techniques to improve the accuracy of the estimation performed by the diffusion weight model 251.

The diffusion weight model 251 measures the diffusion of scientific evidence and models the opinion spreading mechanism across scientists and clinicians in the network, allowing for a quantification of impact of scientific opinion (e.g., from the scientists) on clinical opinion (e.g., to the clinicians). The diffusion weight model 251 can be configured to estimate diffusion rates between nodes of the heterogenous network and store the weights in a data structure associated with the edges of the heterogenous network. For example, the diffusion weights can be stored in a matrix for each coefficient (e.g., A=[$A_{ij}$], B=[$B_{ij}$] and C=[$C_{ij}$]) and embedded into data structures for the edges of the heterogenous network. In some implementations, diffusion weights can be embedded into the nodes of the heterogenous network, e.g., as node features, node attributes.

Figure 3A:
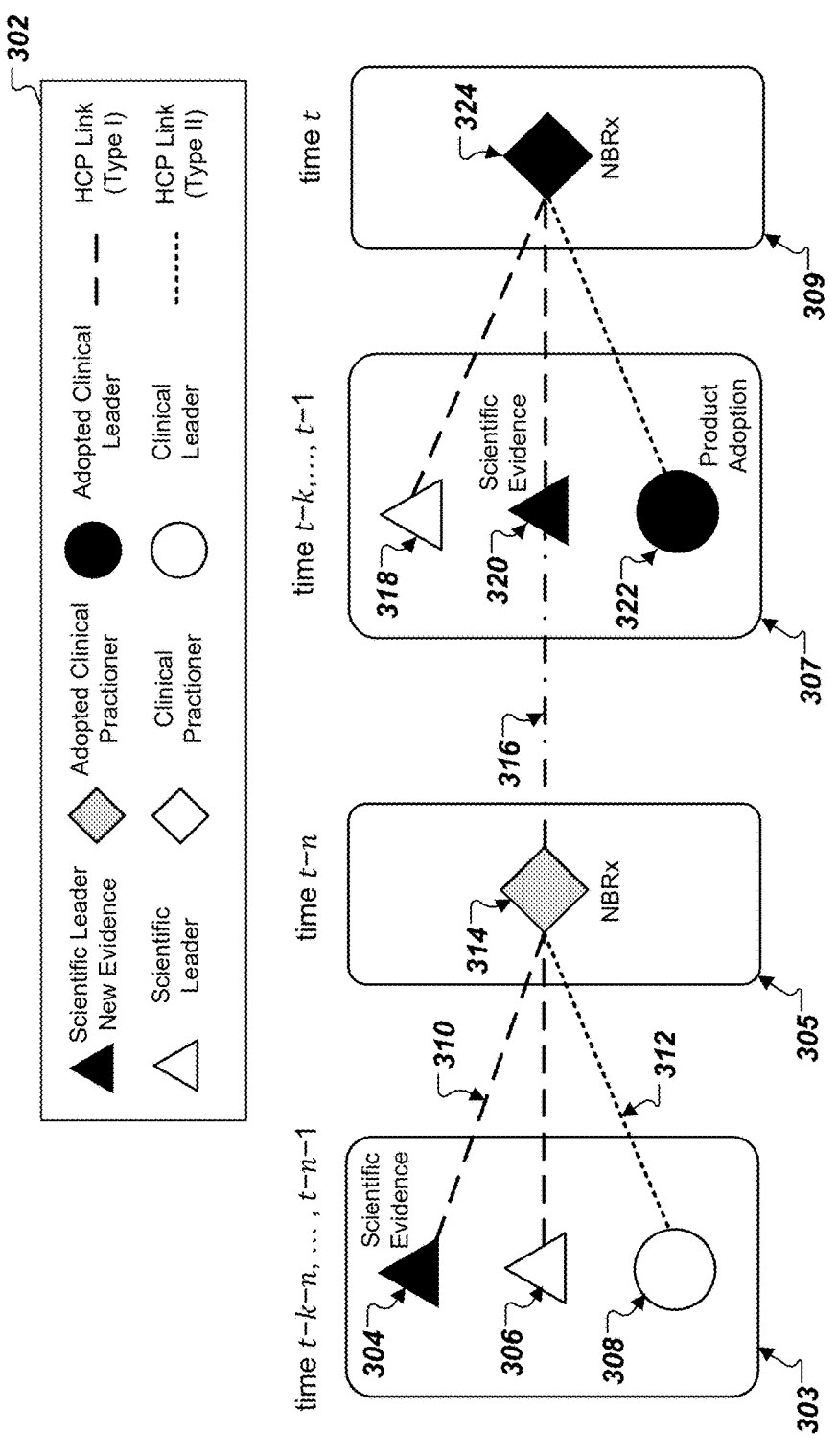
FIG. 3A is a block diagram that illustrates an example quantification of evidence impact throughout a heterogenous network.

FIG. 3A is a block diagram 300 that illustrates an example quantification of evidence impact throughout a heterogenous network. The diagram 300 can be an example quantification of the impact of scientific evidence on HCP prescription adoption, e.g., the adoption of particular medications and/or therapies from scientific evidence that is adopted by a clinical HCP. The diagram 300 illustrates a dynamic system for measuring knowledge diffusion through the nodes of the heterogenous network, as performed by the system 100 of FIG. 1 referenced above. The system 100 can be used to model a historical diffusion of scientific evidence throughout the heterogenous network through diffusion weights between nodes of the heterogenous network, but can also be used to predict future diffusion of scientific information.

The diagram 300 shows a legend 302 indicating different types of events, impacts, or actors modeled by the heterogenous network that can be correlated to time series data, e.g., to quantify the spread of a piece of evidence occurring at a single time instance or over multiple time instances. A time-varying diffusion model can be represented at different stages to measure adoption volume of scientific evidence, indicated by reference numerals 303, 305, 307, 309 (also referred to as "stage 303," "stage 305," "stage 307," "stage 309," respectively). For example, stage 303 shows a scientific leader 304 that introduces a new piece of scientific evidence (indicated by a triangle with a solid, black fill) at the time instance time t–k–n, . . . , t–n–1, where t is the present time of the estimation for adoption volume, and k is a historical time period (e.g., 6 months). Along with the scientific leader 304 introducing new evidence, a scientific leader 306 (indicated by a triangle with a solid, white fill) and a clinical leader 308 (indicated by a circle with a solid, white fill) are shown for reference, and can be candidates of potential diffusion of the scientific evidence introduced by the scientific leader 304.

At stage 305 corresponding to time t–n, a measure of treatment decisions from an adopted clinical practitioner 314 can be measured, and multiple types of links can be generated to quantify the influence of practitioners from the previous stage 303. The adopted clinical practitioner 314 is a clinical practitioner in the heterogenous network who can be a candidate of a HCP adopting a treatment, medication, and/or therapy referenced by the piece of scientific evidence introduced by scientific leader 304 at stage 303.

Different types of HCP links can be established between HCPs at different stages of the diffusion model for the heterogenous network. For example, a first type of HCP link can indicate influence between two different types of health-care providers (e.g., scientific HCP to clinician HCP, clinician HCP to scientific HCP). between scientific leader 304 in stage 303 (who introduced the piece of scientific evidence) and the adopted clinical practitioner 314 in 305 (who prescribed a number of medications, therapies, or performed a number of treatments associated with the piece of scientific evidence). The diagram 300 shows a link 312 between the scientific leader 304 and the adopted clinical practitioner 314, indicating influence between the two different types of HCPs, e.g., to track the impact of the piece of scientific evidence. A second type of HCP link can indicate influence between two HCPs of the same type (e.g., scientific HCP to scientific HCP, clinician HCP to clinician HCP), as shown by link 312 between the clinical leader 308 at stage 303 and the adopted clinical practitioner 314 at stage 305. This can helpful, as clinical leaders can influence other members in a heterogenous network (e.g., a clinician, a scientists) to adopt a piece of scientific evidence, e.g., the scientific evidence introduced by the scientific leader 304. In some cases, clinical leaders can influence scientists based on adopted treatments or treatment provided to patients, e.g., to direct research performed by scientists towards a particular treatment. In this way, knowledge diffusion from clinical leaders to scientific leaders and/or other clinical leaders can be quantified.

The diagram 300 also shows a link 316 (illustrated as a line with a dash-dot pattern) between the adopted clinical practitioner 314 at stage 305 and another scientific leader 320 introducing a new piece of scientific evidence at stage 307, e.g., a piece of evidence different than the piece of evidence introduced by scientific leader 304 at stage 303. The link 316 shows that the two pieces of evidence from scientific leaders 304 at stage 303 and scientific leader 320 at stage 307 can refer to the same treatment, therapy, medication, etc., that is administered by the adopted clinical practitioner 314 at stage 305. In this way, the system 100 of FIG. 1 can track the administration of treatment decisions performed by clinicians to help identify the spread and adoption of new treatments, medications, etc., that is originally introduced by a scientist.

The stage 307 shows the second piece of scientific evidence from the scientific leader 320 introduce at some time instance in a range of times instances, (e.g., time t–k, . . . , t–1), and other nodes of the heterogenous network, such as the scientific leader 318 and the adopted clinical leader 322. At stage 307, a time instance can be identified in which product adoption for a particular medication, treatment, therapy, etc., occurs, as indicated by adopted clinical leader 322. The occurrence of product adoption by a clinical leader (such as clinical leader 322 of stage 307) can indicate that a number of treatment decisions by clinicians exceeds a threshold number. In this way, the influence of one or more pieces of scientific evidence that reference the adopted product (e.g., treatment, medication) can indicate a successful adoption of research by clinicians of the heterogenous network.

At stage 309, an adopted clinical practitioner 324 at time instance t is shown as adopting the treatment from the scientific evidence through a number of treatment decisions (e.g., measured as NBRx). Links connecting the adopted clinical practitioner 324 at stage 309 to clinical practitioners and scientific leaders at stage 307 can indicate the type of influence, e.g., whether the diffusion of information is from a node with the same HCP type, as well as a quantification of how much influence the node to the adopted clinical practitioner 324 has for treatment decisions.

Figure 3B:
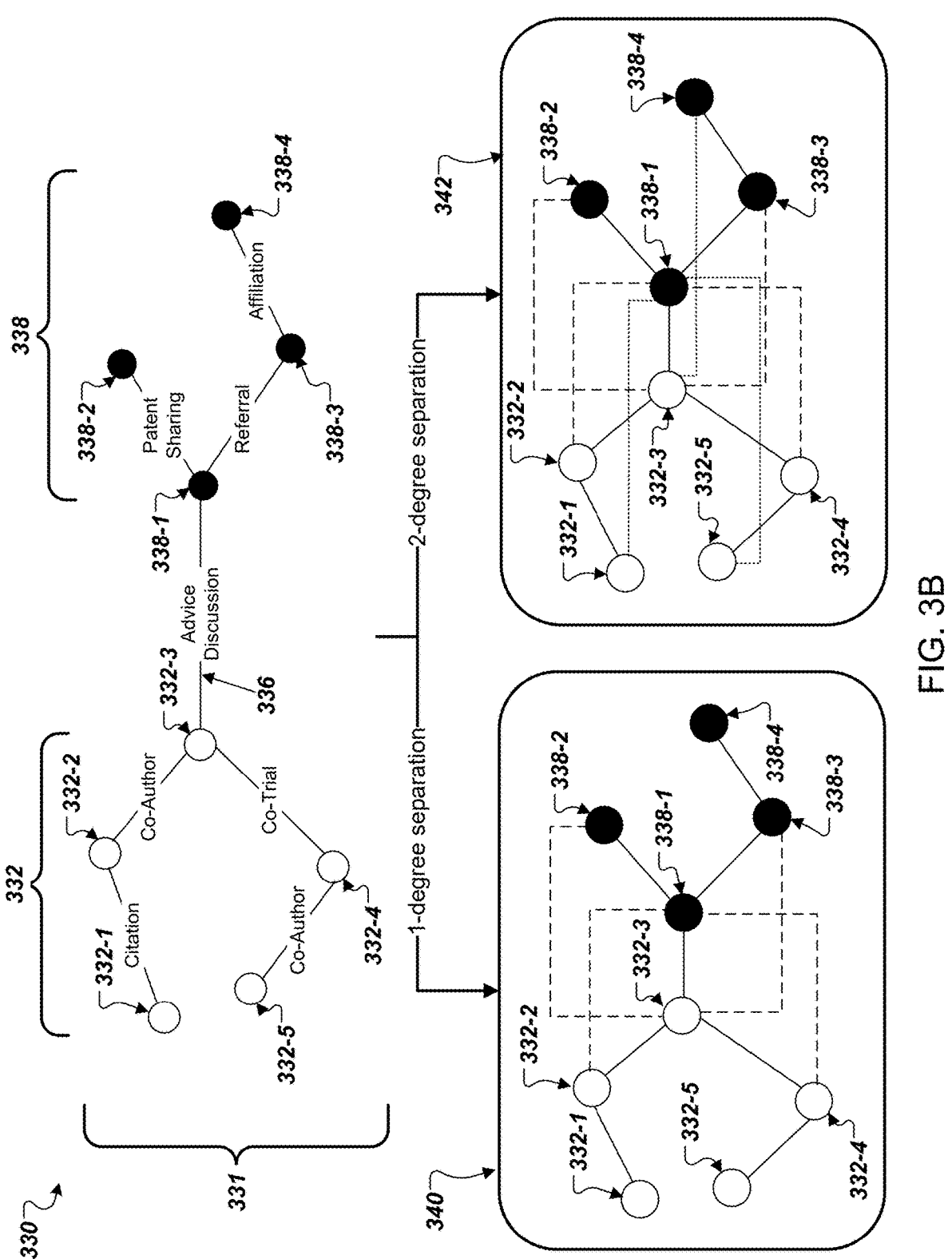
FIG. 3B is a block diagram that illustrates an example of degree expansion for a heterogenous network.

FIG. 3B is a block diagram 330 that illustrates an example of degree expansion for a heterogenous network 331. The degree expansion for the heterogenous network can be performed by the system 100, e.g., through the computing device 121 and the link prediction engine 132. The degree of a node is a number of edges that are connected to the node, and an n degree expansion of a node can include adding nodes and edges to the heterogenous network until the heterogenous network is connected to at least n new nodes. Through the link prediction engine 132, the system 100 expands the degrees of the nodes in the heterogenous network to increase connectivity, thereby increasing the likelihood of generating links between different types of nodes in the heterogenous network, e.g., links between nodes for clinician HCPs and scientific HCPs. In some implementations, n-degree expansion connects nodes to a particular node (including nearest neighbors of a node) up to an n'h degree of separation. Through expanding the nodes of the heterogenous network, the system 100 increases the accuracy of connections between nodes representing HCPs of the heterogenous network and quantification of influence resulting from the connection of the nodes for the HCPs.

The block diagram 330 shows the heterogenous network 331 that includes a scientific network 332 having scientist nodes 332-1 through 332-5 and includes a clinical network 338 having clinician nodes 338-1 through 338-4. Each edge between nodes in the heterogenous network 331 show the relationship between HCPs (clinical or scientific) and how the relationship is established. For example, scientist node 332-1 connects to a scientific node 332-2 with an edge indicating the association of the two scientists being a citation, e.g., on a piece of scientific evidence such as a publication. As another example, clinician node 331-1 connects to clinician node 338-3 through an edge indicating the association of the two clinicians being a referral, e.g., one clinician refers patients to the other clinician. The connection of the nodes can indicate that a level of influence can be quantified, e.g., a normalized value generated by the diffusion weight model 251 indicating an amount of influence one HCP has on another HCP. The diagram 330 shows a link 336 represented as an edge of the heterogenous network 331 connecting the scientific node 332-3 and the clinician node 338-1, with the edge indicating an advice session between the corresponding HCPs of the nodes as the association between the HCPs. The link 336 is a link generated by the link prediction engine 132, described above in reference to FIGS. 1A and 1B.

The block diagram 330 shows a first-degree expansion 340 of the heterogenous network 331, in which the dashed lines indicate possible links between nodes of the heterogenous network. As depicted in FIG. 3B, the first-degree expansion 340 shows a potential link between scientific node 332-2 and clinician node 338-1, between scientific node 332-3 and clinician node 338-2, between scientific node 332-2 and clinician node 338-3, and between scientific node 332-4 and clinician node 338-1. The block diagram 330 shows a second-degree expansion 342 of the heterogenous network, in which the dotted lines indicate possible links between nodes of the heterogenous network 331. The second-degree expansion 342 of the heterogenous network 331 also includes links from the first-degree expansion 340 of the heterogenous network 331. As depicted in FIG. 3B, the second-degree expansion 342 shows a potential link between scientific node 332-1 and clinician node 338-1, between scientific node 332-3 and clinician node 338-4, and between scientific node 332-5 and clinician node 338-1. The link prediction engine 132 can be configured to process feature data of nodes identified in the degree expansion of the heterogenous network 331 and predict additional links between nodes of the heterogenous network 331, e.g., increasing the likelihood of capturing influence between different types of HCPs and to quantify diffusion of scientific information.

Figure 3C:
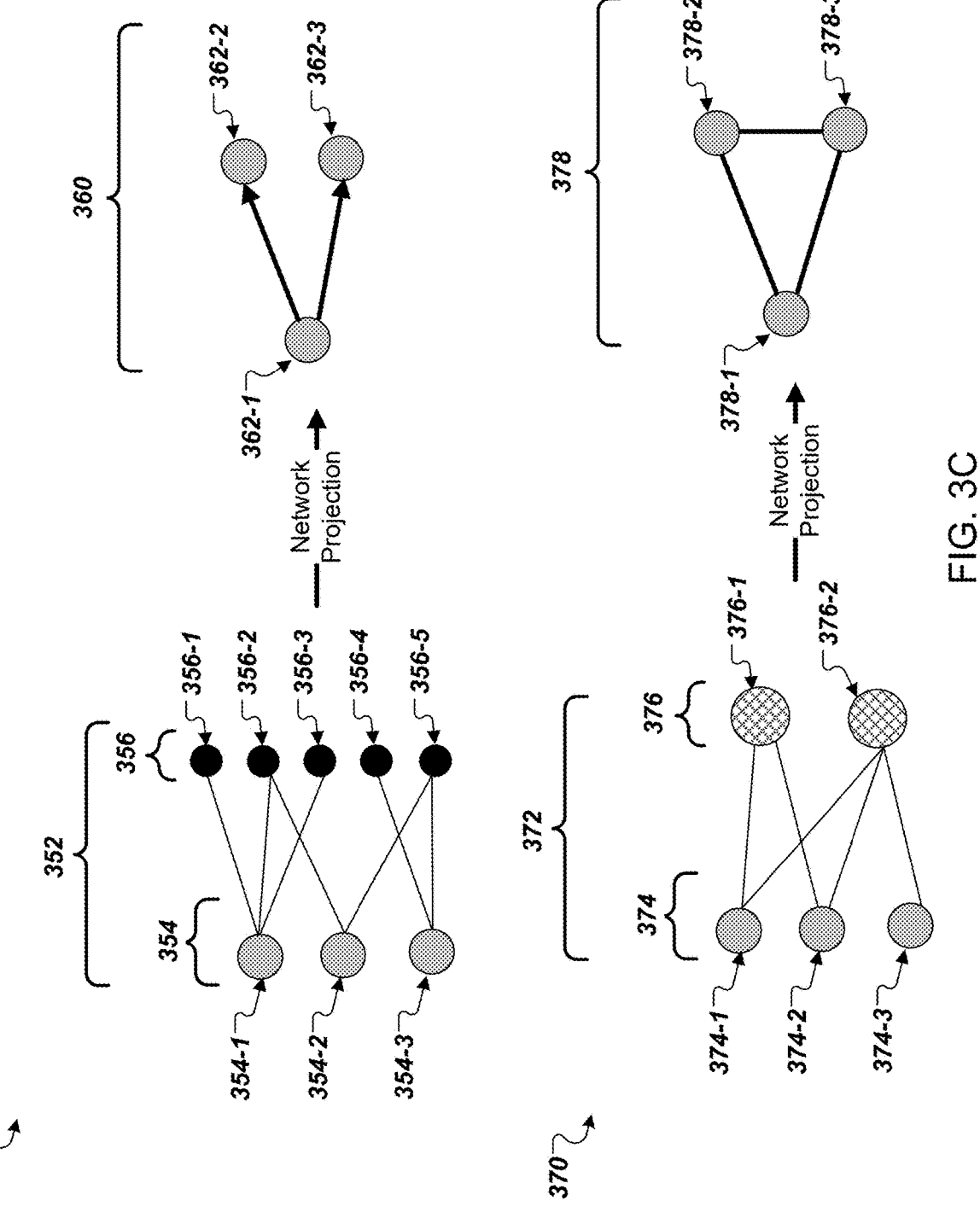
FIG. 3C is a block diagram that illustrates example network projections of bipartite graphs.

FIG. 3C illustrates block diagrams 350 and 370 that illustrates example network projections of bipartite graphs. The system 100 of FIG. 1A can perform network projections of bipartite graphs that relate clinicians and/or scientists to other types of data represented as nodes, such as patients and research organizations, respectively. In this way, performing a network projection to construct a graph network (e.g., a heterogenous network) provides that diffusion weights determined from the graph network are more accurate measures of diffusion intensity between healthcare providers of the graph network, e.g., compared to approaches without performing network projection.

The system 100 can perform network projection by applying a number of techniques. For example, the computing device 121 can include a graph neural network configured to learn node embeddings in a graph network, e.g., by aggregating and processing feature data from the nodes. The graph neural network can be trained to perform an embedding process, which includes a projection of data from a first dimensional space into a second dimensional space smaller than the first dimensional space. By doing so, the system 100 can achieve substantial computational resource savings, as the embeddings of node features are computationally efficient data structures, and optionally, can include selecting subsets of the node feature data, e.g., in contrast to processing all of the feature data for a node. In some implementations, network projection can include projecting nodes with similar features, or within a proximity to one another, to be in a similar projection space and thus providing a compact representing of the graph network, e.g., to reduce consumption of computational resources.

The block diagram 350 shows a patient centric network 352 that includes connections between HCP nodes 354 representing healthcare providers (also referred to as "HCP nodes 354"), which include HCP node 354-1, HCP node 354-2, and HCP node 354-3, and patient nodes 356 corresponding to patients of the HCPs. The patient nodes 356 include patient node 356-1 through patient node 356-5. The block diagram 350 shows that the HCP nodes 354 and patient nodes 356 can be bi-partite graphs, e.g., nodes can be grouped into two disjoint sets of nodes and edges only connect nodes between the two disjointed sets of nodes. In this case, the HCP nodes 354 are a first disjoint set and the patient nodes 356 are a second disjoint set. The system 100 of FIG. 1A can be configured to perform a network projection of the patient centric network 352 to form a unipartite HCP network 360. The unipartite HCP network 360 includes HCP nodes 362-1 through 362-3 and can describe patient sharing, referral networks, and other patient-centric relationships between HCPs into an HCP-centric network, e.g., the unipartite HCP network 360.

Similarly, the block diagram 370 shows an affiliation-research centric network 372 that includes connections between HCP nodes 374 representing healthcare providers (also referred to as "HCP nodes 374"), which include HCP node 374-1, HCP node 374-2, and HCP node 374-3. The affiliation-research centric network 372 also includes organization nodes 376 corresponding to affiliated organizations for the HCPs. The organization nodes 376 include organization node 376-1 and organization node 376-2. The block diagram 370 shows that the HCP nodes 374 and organization nodes 376 can be bi-partite graphs with the HCP nodes 374 being a first disjoint set and the organization nodes 376 being a second disjoint set. The system 100 of FIG. 1A can be configured to perform a network projection of the affiliation-research centric network 372 to form a unipartite HCP network 378. The unipartite HCP network 378 includes HCP nodes 378-1 through 378-3 and can describe co-authorship, affiliations, and other types of affiliation-research associations between HCPs and their affiliates into an HCP-centric network, e.g., the unipartite HCP network 378.

FIG. 4A is a flow diagram that illustrates an example of a process 400 for generating heterogeneous networks for measuring diffusion of scientific information. The process 400 can be performed by computing devices and/or systems, such as the diffusion network system 100 and computing device 121 illustrated in FIG. 1A. The process 400 can be performed to generate a heterogenous network (e.g., heterogenous network 134 of FIG. 1A), from different types of data sources, such as clinical data (e.g., clinical data sources 102) and scientific data (e.g., scientific data sources 104).

The process 400 includes obtaining clinical data associated with a clinical network of healthcare providers. The clinical data includes treatment information for patients of the healthcare providers (402). In some implementations, the clinical data is obtained from a plurality of clinical data sources, the plurality of clinical data sources including at least one of (i) medical claims, (ii) prescription claims, (iii) healthcare provider demographic data, (iv) medical products, or (v) medical procedures.

The process 400 includes obtaining scientific data associated with a scientific network of scientists. The scientific data is indicative of scientific publications associated with the scientists (404). In some implementations, the scientific data is obtained from a plurality of scientific data sources, the plurality of scientific data sources including at least one of (i) clinical trials, (ii) research studies, (iii) patents, (iv) grants, (v) conference presentations, (vi) publications, (vii) treatment guidelines.

The process 400 includes generating, from the clinical data, a first graph network representing the clinical network and indicative of influence between different healthcare providers of the healthcare providers (406). The first graph network includes first nodes and first edges, each first node representing a corresponding healthcare provider from the healthcare providers, each first edge connecting two first nodes and indicative of influence between the corresponding healthcare providers of the connected first nodes. In some cases, the first graph network is generated by machine learning models, which can include deep learning models, graph based models (e.g., graph-based clustering, graph neural networks, graph convolutional networks, among other types of networks). The machine learning models can perform predictive modeling to generate the first graph network from the clinical data sources.

The first graph network (also referred to as "the clinical network") can be generated by analyzing shared patients, referral relationships, among other types of relationships between clinicians, based on the clinical data. Key opinion leaders can be determined by identifying nodes corresponding to clinicians with a higher degree, e.g., a number of connections to other clinicians. In some cases, clinical key opinion leaders can be determined based on an importance of their role in a clinical network, e.g., the professional level of the clinician is higher in an organizational hierarchy relative to the professional level of another clinician.

In some implementations, the first graph network of the clinical network includes one or more identified clinical subnetworks, each identified clinical subnetwork being one of (i) a patient sharing network, (ii) a referral network, (iii) an alumni network, (iv) a referral network, or (v) an advice peer network.

The process 400 includes generating, from the scientific data and using a machine learning engine, a second graph network representing the scientific network and indicative of influence between different scientists of the scientists (408). The second graph network includes second nodes and second edges, each second node representing a corresponding scientist from the scientists, each second edge connecting two second nodes and indicative of influence between the corresponding scientists of the connected second nodes. The second graph network (also referred to as "the scientific network") can be generated by analyzing co-authorship, co-presenting, co-trial relationships (among other relationships) between scientists in the scientific network, based on the scientific data (e.g., publications, presentations, and clinical trials). Scientific key opinion leaders can be determined by determining scientists with relative high volumes of research activity, e.g., number of presentations, number of publications, number of trials, number of citations. In some cases, scientific key opinion leaders can be determined based on a position of the scientist in the scientific network, e.g., the node representing a scientist has a higher centrality measure than other nodes in the network. Examples of centrality measures can include degree centrality, betweenness centrality, closeness centrality, among others.

In some implementations, the machine learning engine includes at least one of (i) a large language model, or (ii) a natural language processing model.

In some implementations, the second graph network of the scientific network includes one or more identified scientific subnetworks, each identified scientific subnetwork being one of (i) a co-authorship network, (ii) a citation network, (iii) a co-trial participants network, or (iv) co-conference presenters network.

In some implementations, generating the second graph network includes generating, by the machine learning engine, one or more mappings between the scientific publications associated with the scientists and the healthcare providers of the clinical network. Each of the one or more mappings represents an influence of a respective scientific publication on the respective healthcare provider. In some implementations, the one or more mappings are stored in a data warehouse.

The process 400 includes identifying, using survey data representing healthcare sociometric information of the clinical network and scientific network, a first set of target nodes in the first graph network and a second set of target nodes in the second graph network (410). Each node in the first set of target nodes represents a clinical leader in the clinical network, and each node in the second set of target nodes represents a scientific leader in the scientific network.

In some implementations, the survey data is obtained from surveys of one or both of (i) at least a first subset of the healthcare providers of the clinical network, or (ii) at least a second subset of the scientists of the scientific network.

In some implementations, the clinical leader is a healthcare provider from the clinical network with an amount of influence that exceeds a first threshold value. In some implementations, the scientific leader is a scientist from the scientific network with an amount of influence that exceeds a second threshold value.

The process 400 includes predicting, using the first and second set of target nodes and by a link prediction model, links connecting the first graph network to the second graph network (412). The link prediction model can be the link prediction engine 132 of FIG. 1A and can be trained to predict relationships between two members in the healthcare community, e.g., scientists and/or clinicians. In particular, the link prediction model can be trained by using healthcare provider demographics data, claims data, among other types of clinical data and/or scientific data.

The process 400 includes generating a heterogenous network including third nodes and third edges (414). The third nodes include the first nodes from the first graph network and the second nodes from the second graph network. The third edges include the links connecting the first graph network and the second graph network. In some implementations, the first graph network and the second graph network are bipartite graphs of the heterogenous network.

FIG. 4B is a flow diagram that illustrates an example of a process 450 for determining diffusion of scientific information throughout different healthcare networks. The process 450 can be performed by computing devices and/or systems, such as the diffusion network system 100 and computing device 121 illustrated in FIG. 1A. The process 450 can be measure the diffusion of information in a heterogenous network (e.g., heterogenous network 134 of FIG. 1A).

The process 450 includes determining, from the heterogenous network, a first time instance associated with scientific evidence from the scientific network (452). The first time instance associated with the scientific evidence represents a time instance of a scientific publication being associated with at least a subset of nodes from the third nodes.

The process 450 includes measuring, for each of one or more additional time instances of the heterogenous network and using the links of the heterogenous network associated with at least one of the first set of target nodes or the second set of target nodes, an adoption volume of the scientific evidence for the corresponding healthcare providers from the first set of target nodes (454).

The process 450 includes determining, from the measured adoption volume, a diffusion weight of the scientific evidence for at least one of (i) a link from the links connecting the first graph network to the second graph network, or (ii) each link from the links connecting two connected nodes from the third plurality of nodes of the heterogenous network (456). In some implementations, measuring adoption volume of a piece of scientific evidence includes measuring a number of treatment decisions for the patients of the healthcare providers in the clinical network.

In some implementations, the process 450 includes configuring, by one or more computing devices, the heterogenous network as a model to generate a time-series analysis of adoption of one or more of (i) a piece of scientific evidence, or (ii) a medication, by at least a subset of the healthcare providers or the scientists represented by the third nodes of the heterogenous network. The process 450 can include generating, by the model using the input, an output that is the time-series analysis of adoption volume from the subset of the third nodes.

In some implementations, the time period is a historical time period that occurs prior to the first time instance. The time period can be a future time period that occurs after the first time instance. In some implementations, the model is configured as simulator of adoption volume. In some implementations, the process 450 includes identifying, from the output, the subset of the third plurality of the heterogeneous network having a diffusion rate at least a threshold value.

Figure 5:
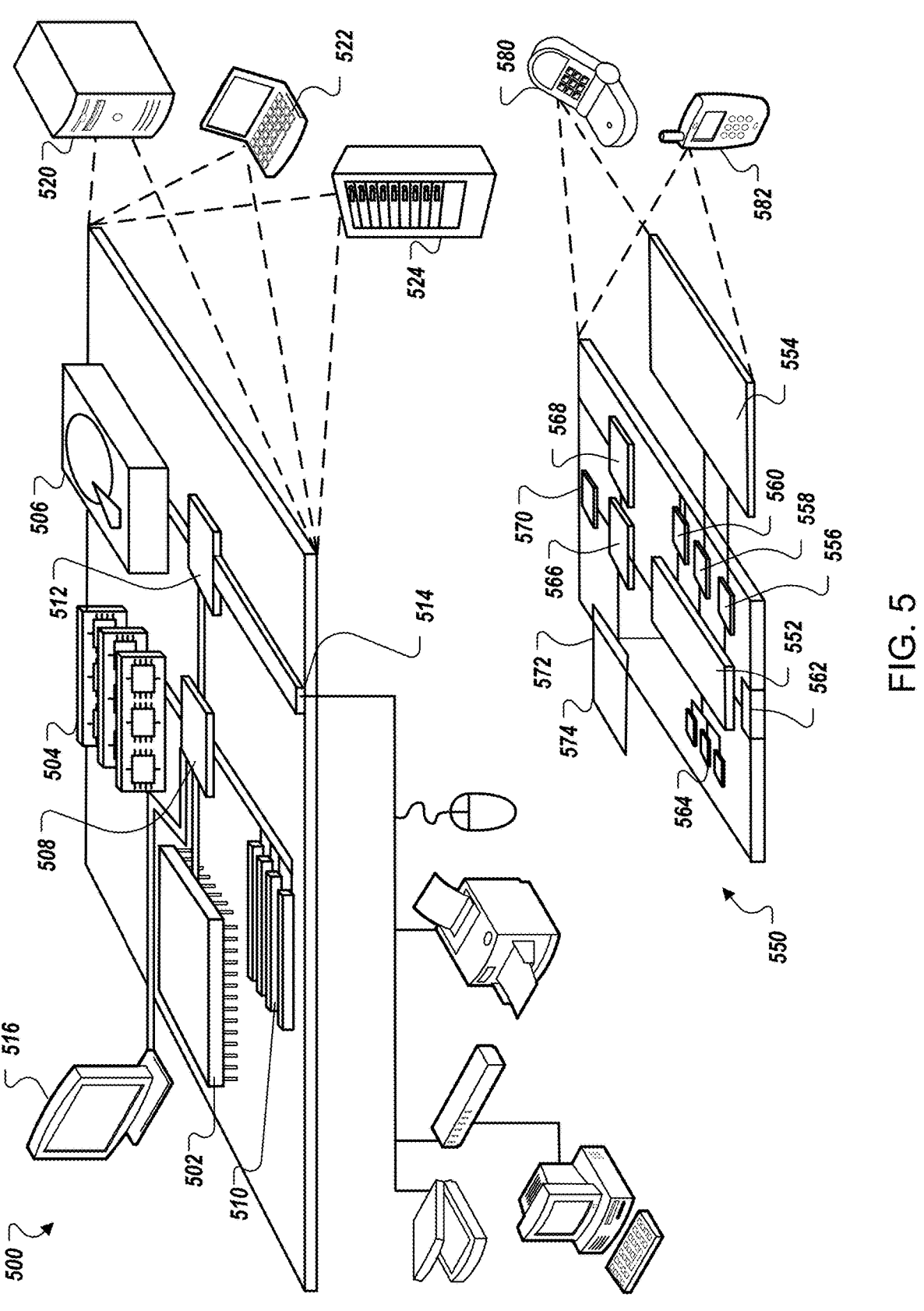
FIG. 5 shows a block diagram of a computing system.

FIG. 5 is a block diagram of computing devices 500, 550 that may be used to implement the systems and methods described in this document, as either a client or as a server or multiple servers. As an example, computing device 121 and/or diffusion network system 100 can be an example of computing devices 500, 550 to generate a heterogenous network and measure diffusion of information in the heterogenous network. Computing device 500 and 550 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations, e.g., as a server bank, a group of blade servers, or a multi-processor system.

The memory 504 stores information within the computing device 500. In one implementation, the memory 504 is a computer-readable medium. In one implementation, the memory 504 is a volatile memory unit or units. In another implementation, the memory 504 is a non-volatile memory unit or units.

The storage device 506 is capable of providing mass storage for the computing device 500. In one implementation, the storage device 506 is a computer-readable medium. In various different implementations, the storage device 506 may be a floppy disk device, a hard disk device, an optical disk device, or a tape device, a flash memory or other similar solid-state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 504, the storage device 506, or memory on processor 502.

The high-speed controller 508 manages bandwidth-intensive operations for the computing device 500, while the low speed controller 512 manages lower bandwidth-intensive operations. Such allocation of duties is exemplary only. In one implementation, the high-speed controller 508 is coupled to memory 504, display 516, e.g., through a graphics processor or accelerator, and to high-speed expansion ports 510, which may accept various expansion cards (not shown). In the implementation, low-speed controller 512 is coupled to storage device 506 and low-speed expansion port 514. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown), such as device 550. Each of such devices may contain one or more of computing device 500, 550, and an entire system may be made up of multiple computing devices 500, 550 communicating with each other.

Computing device 550 includes a processor 552, memory 564, an input/output device such as a display 554, a communication interface 566, and a transceiver 568, among other components. The device 550 may also be provided with a storage device, such as a microdrive or other device, to provide additional storage. Each of the components 550, 552, 564, 554, 566, and 568, are interconnected using various buses, and several of the components may be mounted on a common motherboard or in other manners as appropriate.

The processor 552 can process instructions for execution within the computing device 550, including instructions stored in the memory 564. The processor may also include separate analog and digital processors. The processor may provide, for example, for coordination of the other components of the device 550, such as control of user interfaces, applications run by device 550, and wireless communication by device 550.

Processor 552 may communicate with a user through control interface 558 and display interface 556 coupled to a display 554. The display 554 may be, for example, a TFT LCD display or an OLED display, or other appropriate display technology. The display interface 556 may include appropriate circuitry for driving the display 554 to present graphical and other information to a user. The control interface 558 may receive commands from a user and convert them for submission to the processor 552. In addition, an external interface 562 may be provided in communication with processor 552, so as to enable near area communication of device 550 with other devices. External interface 562 may provide, for example, for wired communication, e.g., via a docking procedure, or for wireless communication, e.g., via Bluetooth or other such technologies.

The memory 564 stores information within the computing device 550. In one implementation, the memory 564 is a computer-readable medium. In one implementation, the memory 564 is a volatile memory unit or units. In another implementation, the memory 564 is a non-volatile memory unit or units. Expansion memory 574 may also be provided and connected to device 550 through expansion interface 572, which may include, for example, a SIMM card interface. Such expansion memory 574 may provide extra storage space for device 550, or may also store applications or other information for device 550. Specifically, expansion memory 574 may include instructions to carry out or supplement the processes described above, and may include secure information also. Thus, for example, expansion memory 574 may be provided as a security module for device 550, and may be programmed with instructions that permit secure use of device 550. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 564, expansion memory 574, or memory on processor 552.

Device 550 may communicate wirelessly through communication interface 566, which may include digital signal processing circuitry where necessary. Communication interface 566 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 568. In addition, short-range communication may occur, such as using a Bluetooth, WiFi, or other such transceiver (not shown). In addition, GPS receiver module 570 may provide additional wireless data to device 550, which may be used as appropriate by applications running on device 550.

Device 550 may also communicate audibly using audio codec 560, which may receive spoken information from a user and convert it to usable digital information. Audio codec 560 may likewise generate audible sound for a user, such as through a speaker, e.g., in a handset of device 550. Such sound may include sound from voice telephone calls, may include recorded sound, e.g., voice messages, music files, etc., and may also include sound generated by applications operating on device 550.

The computing device 550 may be implemented in a number of different forms, as shown in the figure. For example, it may be implemented as a cellular telephone 580. It may also be implemented as part of a smartphone 582, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

What is claimed is:

1. A computer-implemented method performed by one or more computers comprising:

generating, from clinical data associated with a clinical network of healthcare providers, a first graph network representing the clinical network, the first graph network comprising first nodes representing healthcare providers and first edges connecting two first nodes and indicative of influence between the corresponding healthcare providers;

generating, from scientific data associated with a scientific network of scientists and using a machine learning engine, a second graph network representing the scientific network and indicative of influence between different scientists of the scientists, the second graph network comprising second nodes and second edges, each second node representing a corresponding scientist from the scientists, each second edge connecting two second nodes and indicative of influence between the corresponding scientists of the connected second nodes;

identifying, using survey data representing healthcare sociometric information of the clinical network and scientific network, a first set of target nodes in the first graph network and a second set of target nodes in the second graph network, wherein each node in the first set of target nodes represents a clinical leader in the clinical network, and wherein each node in the second set of target nodes represents a scientific leader in the scientific network;

predicting, using the first and second set of target nodes and by a link prediction model, links connecting the first graph network to the second graph network;

generating a heterogenous network comprising third nodes and third edges, wherein the third nodes comprise the first nodes from the first graph network and the second nodes from the second graph network, and wherein the third edges comprise the links connecting the first graph network and the second graph network;

determining, from the heterogenous network, a first time instance associated with scientific evidence, wherein the first time instance represents a time instance of a scientific publication being associated with at least a subset of the third nodes;

measuring, for each of one or more additional time instances of the heterogenous network and using the links of the heterogenous network associated with the first set of target nodes, an adoption volume of the scientific evidence for the corresponding healthcare providers from the first set of target nodes; and determining, from the measured adoption volume, a diffusion weight of the scientific evidence for a link from the links connecting the first graph network to the second graph network.

2. The computer-implemented method of claim 1, wherein measuring adoption volume of the scientific evidence comprises measuring a number of treatment decisions for patients of the healthcare providers in the clinical network.

3. The computer-implemented method of claim 1, further comprising:

generating, by a model configured from the heterogenous network, an output comprising a time-series analysis of adoption of a piece of scientific evidence by the third nodes of the heterogenous network.

4. The computer-implemented method of claim 3, wherein the time period is a historical time period that occurs prior to the first time instance.

5. The computer-implemented method of claim 3, wherein the time period is a future time period that occurs after the first time instance.

6. The computer-implemented method of claim 3, wherein the model is configured as a simulator of adoption volume.

7. The computer-implemented method of claim 3, further comprising:

identifying, from the output, the subset of the third plurality of the heterogeneous network having a diffusion rate at least a threshold value.

8. The computer-implemented method of claim 1, wherein clinical data is obtained from a plurality of clinical data sources, the plurality of clinical data sources comprising (i) medical claims, (ii) prescription claims, (iii) healthcare provider demographic data, (iv) medical products, and (v) medical procedures.

9. The computer-implemented method of claim 1, wherein scientific data is obtained from a plurality of scientific data sources, the plurality of scientific data sources comprising (i) clinical trials, (ii) research studies, (iii) patents, (iv) grants, (v) conference presentations, (vi) publications, and (vii) treatment guidelines.

10. The computer-implemented method of claim 1, wherein the survey data is obtained from surveys of at least a first subset of the healthcare providers of the clinical network.

11. The computer-implemented method of claim 1, wherein the first graph network of the clinical network comprises one or more identified clinical subnetworks, each identified clinical subnetwork being a patient sharing network.

12. The computer-implemented method of claim 1, wherein the second graph network of the scientific network comprises one or more identified scientific subnetworks, each identified scientific subnetwork being a co-authorship network.

13. The computer-implemented method of claim 1, wherein the machine learning engine comprises a natural language processing model.

14. The computer-implemented method of claim 1, wherein the first graph network and the second graph network are bipartite graphs of the heterogenous network.

15. The computer-implemented method of claim 1, wherein the clinical leader is a healthcare provider from the clinical network with an amount of influence that exceeds a first threshold value.

16. The computer-implemented method of claim 1, wherein the scientific leader is a scientist from the scientific network with an amount of influence that exceeds a second threshold value.

17. The computer-implemented method of claim 1, wherein the scientific data is indicative of scientific publications, and wherein generating the second graph network comprises generating, by the machine learning engine, one or more mappings between the scientific publications and the healthcare providers of the clinical network.

18. The computer-implemented method of claim 17, wherein the machine learning engine is trained to perform an inference task comprising text classification and entity identification, wherein the machine learning engine is configured to perform a semantic analysis of the scientific publications by identifying and classifying entities in the scientific publications, and wherein the one or more mappings represent an influence of a respective scientific publication on the respective healthcare provider.

19. A scientific clinical diffusion system comprising:
a computing device comprising at least one processor; and
a memory communicatively coupled to the at least one processor, the memory storing instructions which, when executed by the at least one processor, cause the at least one processor to perform operations comprising:
generating, from clinical data associated with a clinical network of healthcare providers, a first graph network representing the clinical network, the first graph network comprising first nodes representing healthcare providers and first edges connecting two first nodes and indicative of influence between the corresponding healthcare providers of the connected first nodes;
generating, from scientific data associated with a scientific network of scientists and using a machine learning engine, a second graph network representing the scientific network and indicative of influence between different scientists of the scientists, the second graph network comprising second nodes and second edges, each second node representing a corresponding scientist from the scientists, each second edge connecting two second nodes and indicative of influence between the corresponding scientists of the connected second nodes;
identifying, using survey data representing healthcare sociometric information of the clinical network and scientific network, a first set of target nodes in the first graph network and a second set of target nodes in the second graph network, wherein each node in the first set of target nodes represents a clinical leader in the clinical network, and wherein each node in the second set of target nodes represents a scientific leader in the scientific network;
predicting, using the first and second set of target nodes and by a link prediction model, links connecting the first graph network to the second graph network;
generating a heterogenous network comprising third nodes and third edges, wherein the third nodes comprise the first nodes from the first graph network and the second nodes from the second graph network, and wherein the third edges comprise the links connecting the first graph network and the second graph network;
determining, from the heterogenous network, a first time instance associated with scientific evidence, wherein the first time instance represents a time instance of a scientific publication being associated with at least a subset of the third nodes;
measuring, for each of one or more additional time instances of the heterogenous network and using the links of the heterogenous network associated with the first set of target nodes, an adoption volume of the scientific evidence for the corresponding healthcare providers from the first set of target nodes; and
determining, from the measured adoption volume, a diffusion weight of the scientific evidence for a link from the links connecting the first graph network to the second graph network.

20. A non-transitory computer-readable storage device storing instructions that when executed by one or more processors of a computing device cause the one or more processors to perform operations comprising:
generating, from clinical data associated with a clinical network of healthcare providers, a first graph network representing the clinical network, the first graph network comprising first nodes representing healthcare providers and first edges connecting two first nodes and indicative of influence between the corresponding healthcare providers of the connected first nodes;
generating, from scientific data associated with a scientific network of scientists and using a machine learning engine, a second graph network representing the scientific network and indicative of influence between different scientists of the scientists, the second graph network comprising second nodes and second edges, each second node representing a corresponding scientist from the scientists, each second edge connecting two second nodes and indicative of influence between the corresponding scientists of the connected second nodes;
identifying, using survey data representing healthcare sociometric information of the clinical network and scientific network, a first set of target nodes in the first graph network and a second set of target nodes in the second graph network, wherein each node in the first set of target nodes represents a clinical leader in the clinical network, and wherein each node in the second set of target nodes represents a scientific leader in the scientific network;
predicting, using the first and second set of target nodes and by a link prediction model, links connecting the first graph network to the second graph network;
generating a heterogenous network comprising third nodes and third edges, wherein the third nodes comprise the first nodes from the first graph network and the second nodes from the second graph network, and wherein the third edges comprise the links connecting the first graph network and the second graph network;
determining, from the heterogenous network, a first time instance associated with scientific evidence, wherein the first time instance represents a time instance of a scientific publication being associated with at least a subset of the third nodes;
measuring, for each of one or more additional time instances of the heterogenous network and using the links of the heterogenous network associated with the first set of target nodes, an adoption volume of the scientific evidence for the corresponding healthcare providers from the first set of target nodes; and determining, from the measured adoption volume, a diffusion weight of the scientific evidence for a link from the links connecting the first graph network to the second graph network.

* * * * *